United States Patent [19]

Michne

[11] 3,932,422

[45] Jan. 13, 1976

[54] 8-METHYLENE-3-AZABICYCLO[3.3.1]-NON-6-EN-4-ONES

[75] Inventor: William F. Michne, Colonie, N.Y.

[73] Assignee: Sterling Drug Inc., New York, N.Y.

[22] Filed: May 20, 1974

[21] Appl. No.: 471,571

[52] U.S. Cl. ..... 260/293.54; 260/283 R; 260/283 S; 260/287 R; 260/288 R; 260/289 R; 424/267
[51] Int. Cl.² .................................... C07D 221/22
[58] Field of Search .............................. 260/293.54

[56] References Cited
UNITED STATES PATENTS

| | | | |
|---|---|---|---|
| 3,812,134 | 5/1974 | Iwai et al. | 260/293.54 |
| 3,833,595 | 9/1974 | Atsumi et al. | 260/293.54 |

*Primary Examiner*—G. Thomas Todd
*Attorney, Agent, or Firm*—William G. Webb; B. Woodrow Wyatt

[57] ABSTRACT

6(eq)-$R_4$-1,2,3,4,5,6-Hexahydro-3-$R_1$-11(ax)-$R_3$-11(eq)-$CH_2Z$-2,6-methano-3-benzazocines, useful as analgesic agents and narcotic antagonists, and 1-$R_1$-2-Q-4a$\alpha$-$R_3$-5$\alpha$-$R_4$-1,2,3,4,4a,5,10,10a-octahydro-3,5-etheno- (and 3,5-ethano) benzo[g]quinolines, useful as analgesic agents, prepared by heating, with formic acid in an organic solvent or with certain ammonium formates in the absence of a solvent, certain 1,2,3,4,4-a,5,10,10a-octahydro-2,5-methanobenzo[g]quinolines, the latter prepared by acid catalyzed cyclization of a 3-benzyl-2-azabicyclo[2.2.2]oct-5-ene.

3 Claims, No Drawings

8-METHYLENE-3-AZABICYCLO[3.3.1]NON-6-EN-4-ONES

This invention has, as its ultimate object, the obtainment of a new class of chemical compounds, useful as analgesics and narcotic antagonists, having the formula I:

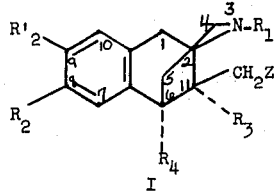

and chemically designated 8-$R_2$-9-$R'_2$-6(eq)-$R_4$-1,2,3,4,5,6-hexahydro-3-$R_1$-11(ax)-$R_3$-11(eq)-$CH_2Z$-2,6-methano-3-benzazocines.

The new 8-$R_2$-9-$R'_2$-6(eq)-$R_4$-1,2,3,4,5,6-hexahydro-3-$R_1$-11(ax)-$R_3$-11(eq)-$CH_2Z$-2,6-methano-3-benzazocines of formula I and other novel intermediates useful in their preparation are obtained according to my invention by novel reactions, including molecular rearrangements involving novel intermediates, according to the general reaction sequence as follows:

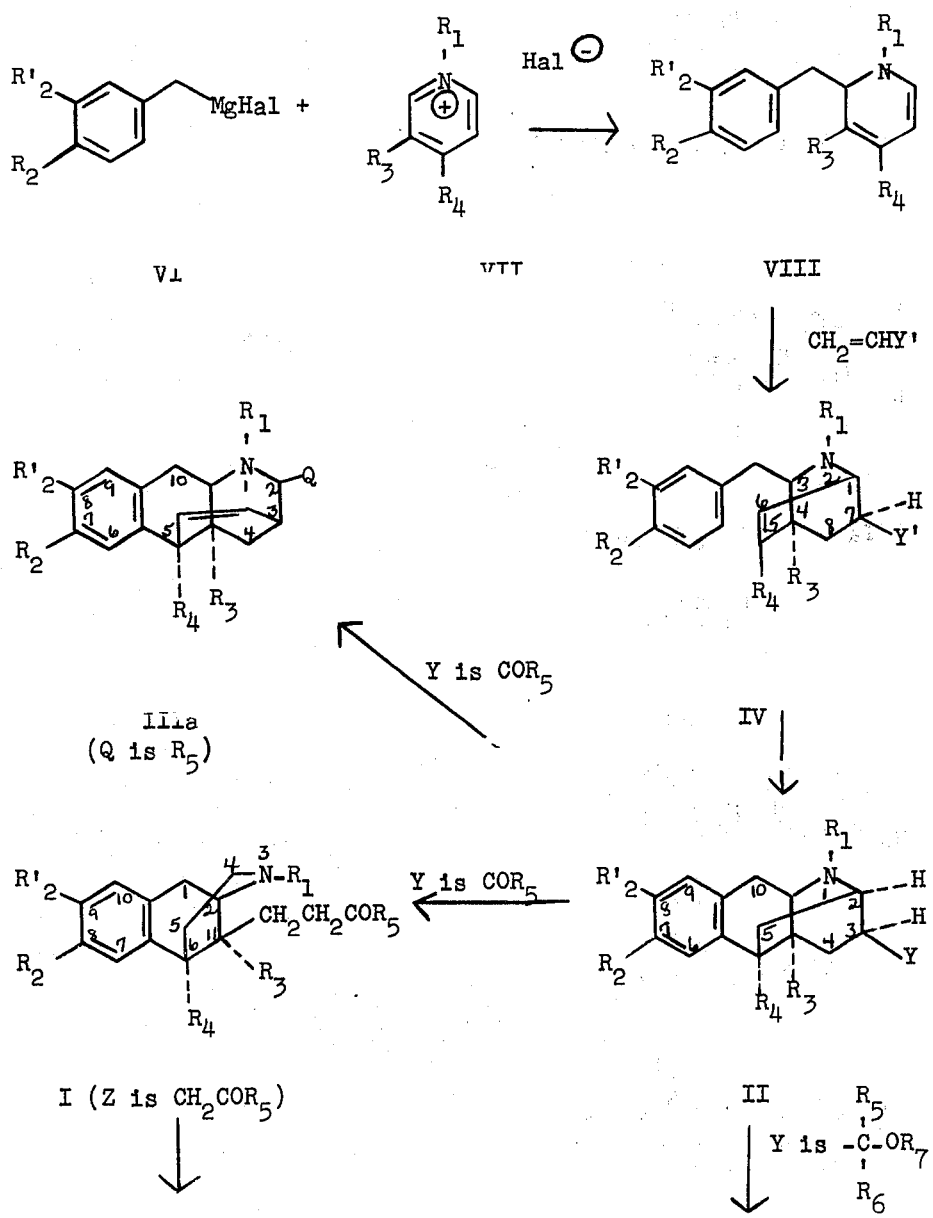

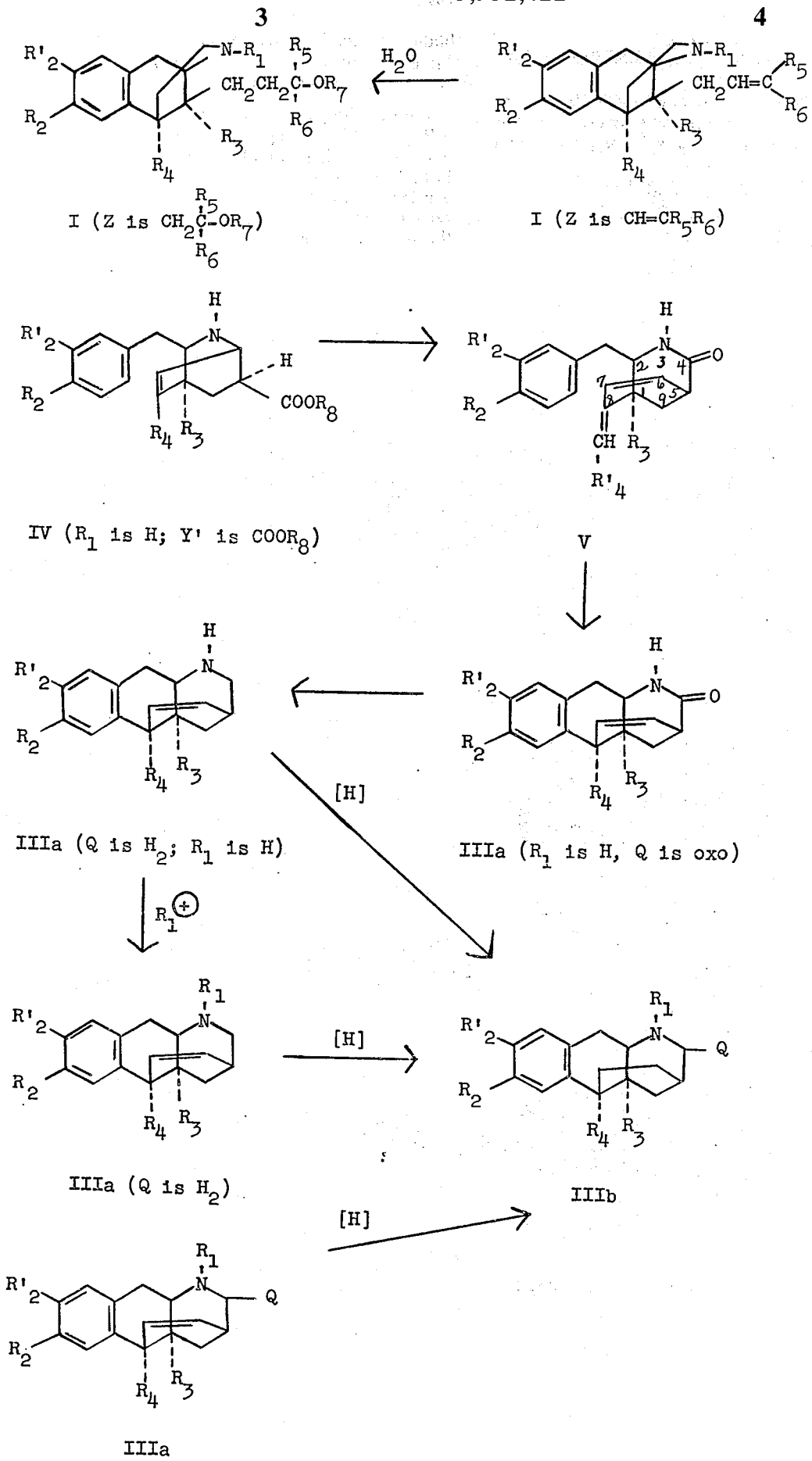

Thus the 8-$R_2$-9-$R'_2$-6(eq)-$R_4$-1,2,3,4,5,6-hexahydro-3-$R_1$-11(ax)-$R_3$-11(eq)-$CH_2Z$-2,6-methano-3-benzazocines having the formula I are prepared via any of several methods from the intermediate 7-$R_2$-8-$R'_2$-1-$R_1$-3-Y-4aα-$R_3$-5α-$R_4$-1,2,3,4,4a,5,10,10a-octahydro-2,5-methanobenzo[g]quinolines of formula II, which themselves are obtained from the 2-$R_1$-3-(4-$R_2$-3-$R'_2$-benzyl)-4-$R_3$-5-$R_4$-7-Y'-2-azabicyclo[2.2.2]oct-5-enes of formula IV which, in turn, are prepared according to standard procedures by reaction of a Grignard reagent derived from a 4-$R_2$-3-$R'_2$-benzyl halide of formula VI with a 3-$R_3$-4-$R_4$-1-$R_1$-pyridinium halide of formula VII and reaction of the resulting 2-(4-$R_2$-3-$R'_2$-benzyl)-3-$R_3$-4-$R_4$-1,2-dihydropyridine of formula VIII with a dienophile, $CH_2$=CHY'. The 7-$R_2$-8-$R'_2$-1-$R_1$-2-Q-4aα-$R_3$-5α-$R_4$-1,2,3,4,4a,5,10,10a-octahydro-3,5-ethenobenzo[g]quinolines of formula IIIa are obtained along with certain compounds of formula I from the compounds of formula II, and the compounds of formula IIIa are also obtainable by rearrangement of a 3-(4$R_2$-3-$R'_2$-benzyl)-4-$R_3$-5-$R_4$-2-azabicyclo[2.2.2]oct-5-ene-7-carboxylic ester of formula IV to a 1-$R_3$-2-(4-$R_2$-3-$R'_2$-benzyl)-8-lower-alkylidene-3-azabicyclo[3.3.1]non-6-en-4-one of formula V and cyclization of the latter to a 7-$R_2$-8-$R'_2$-2-oxo-4aα-$R_3$-5α-$R_4$-1,2,3,4,4a,5,10,10a-octahydro-3,5-ethenobenzo[g]quinoline having the formula IIIa. The compounds of formula IIIa can be catalytically reduced to the 7-$R_2$-8-$R'_2$-1-$R_1$-2-Q-4aα-$R_3$-5α-$R_4$-1,2,3,4,4a,5,10,10a-octahydro-3,5-ethanobenzo[g]quinolines of formula IIIb.

In the final products and intermediates depicted in the above reaction sequences:

$R_1$ is hydrogen, lower-alkyl, lower-alkenyl, lower-alkynyl, halo-lower-alkenyl, cycloalkyl, cycloalkyl-lower-alkyl, phenyl-lower-alkyl, or phenyl-lower-alkyl substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms;

$R_2$ and $R'_2$ each are hydrogen, halogen (including bromine, chlorine or fluorine), lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or $R_2$ and $R'_2$ together are methylenedioxy;

$R_3$ is hydrogen or lower-alkyl;

$R_4$ is hydrogen, lower-alkyl, lower-alkoxy-lower-alkyl, hydroxy-lower-alkyl, lower-alkylthio-lower-alkyl, lower-alkylsulfinyl-lower-alkyl, phenylthio-lower-alkyl, phenylsulfinyl-lower-alkyl, lower-alkenyl or halo-lower-alkyl, or $R_3$ and $R_4$ together are divalent lower-alkylene, —$(CH_2)_n$—, where n is one of the integers 3 or 4;

$R'_4$ is hydrogen or lower-alkyl;

Z is one of the groups —$CH_2COR_5$,

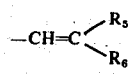

or a group of the formula:

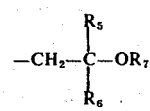

where $R_5$ and $R_6$ are the same or different hydrogen, lower-alkyl, phenyl, or phenyl-lower-alkyl;

$R_7$ is hydrogen, lower-alkanoyl, benzoyl, or benzoyl substituted by from one to three members of the group consisting of lower-alkyl, lower-alkoxy, hydroxy, halo (including chlorine, bromine and fluorine) or trifluoromethyl;

$R_8$ is lower-alkyl, cycloalkyl-lower-alkyl or phenyl-lower-alkyl;

Q is oxo (=O), $H_2$,

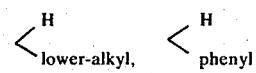

or

Y is carboxy, cyano, carbo-lower-alkoxy, $COR_5$, COO—lower-alkylene-cycloalkyl, COO-lower-alkylene-phenyl, or a group of the formula:

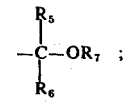

Y' is carboxy, cyano, carbo-lower-alkoxy or lower-alkanoyl: and Hal is halogen.

As used herein, the terms lower-alkyl or lower-alkoxy mean saturated, acyclic groups which may be straight or branched containing from one to about four carbon atoms as exemplified by methyl, ethyl, propyl, isopropyl, butyl, non-adjacent t-butyl, methoxy, ethoxy, propoxy, isopropoxy, or t-butoxy.

As used herein, the terms lower-alkenyl, halo-lower-alkenyl and lower-alkynyl represent monovalent groups of from three to six carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl, and the like. The term halo-lower-alkenyl includes, for example, 2-chloroethenyl, 2-bromoethenyl, 3,3-dichloro-2-propenyl, 1-bromo-2-methylpropenyl, and the like.

As used herein, the term cycloalkyl means saturated carbocyclic groups containing from three to 6 ring carbon atoms as illustrated, for example, by cyclopropyl, cyclobutyl, cyclopentyl, cyclohexyl, 2-methylcyclobutyl, 4-ethylcyclohexyl, and the like.

As used herein, the term lower-alkanoyl means such groups derived from saturated, aliphatic monocarboxylic acids having from 1 to 4 carbon atoms, as illustrated, for example, by formyl, acetyl, propionyl, butyryl, isobutyryl, and the like.

As used herein, the term lower-alkylene means a saturated, divalent radical, which can be straight or branched, and having from one to four carbon atoms, as illustrated, for example, by methylene [—$CH_2$—], 1,2-ethylene [—$CH_2CH_2$—], 1,3-propylene [—$CH_2CH_2CH_2$—], 1,2-(1-methylethylene)- [—$CH(CH_3)CH_2$—], 1,4-butylene [—$CH_2CH_2CH_2CH_2$—], and the like.

As determined by standard pharmacological test procedures to be described hereinafter, the compounds of formula I have been found to have useful analgesic activity, and as disclosed following Example 35B infra, some have been found to have useful narcotic antagonist activity. The compounds of formula I are thus useful as analgesic agents and narcotic antagonists. The compounds of formula III have also been found to have analgesic activity.

In accordance with the above general description, the 8-$R_2$-9-$R'_2$-6(eq)-$R_4$-1,2,3,4,5,6-hexahydro-3-$R_1$-11(ax)-$R_3$-11(eq)-$CH_2Z$-2,6-methano-3-benzazocines of formula I where Z is $CH_2COR_5$

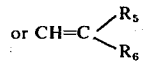

and $R_1$, $R_2$, $R'_2$, $R_3$, $R_4$, $R_5$ and $R_6$ have the meanings given above are prepared by heating, with formic acid in an organic solvent, for example toluene, xylene or mesitylene, or with a benzyl-di-lower-alkylammonium or a tri-lower-alkylammonium formate, a 7-$R_2$-8-$R'_2$-1-$R_1$-3-Y-4a$\alpha$-$R_3$-5$\alpha$-$R_4$-1,2,3,4,4a,5,10,10a-octahydro-2,5-methanobenzo[g]quinoline of formula II where Y is either $COR_5$ (to give the compounds of formula I where Z is $CH_2COR_5$) or the group:

where $R_7$ is hydrogen to give the compounds of formula I where Z is

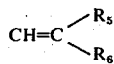

A preferred solvent is mesitylene. The compounds of formula II where Y is $COR_5$ or the group

where $R_7$ is hydrogen are thus intermediates for preparing the compounds of formula I where Z is, respectively, the groups —$CH_2COR_5$ or

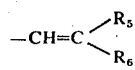

The compounds of formula I where Z is the group:

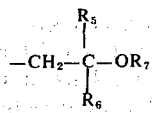

where $R_7$ is hydrogen and $R_5$ and $R_6$ have the meanings given above are prepared from the corresponding compounds where Z is the group

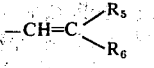

by hydroxylation of the latter with aqueous sulfuric acid and hydrolysis of the resulting hydrogen sulfate ester. The compounds of formula I where Z is the group

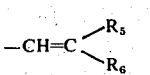

are thus intermediates for the carbinols of formula I.

The compounds of formula I where Z is the group

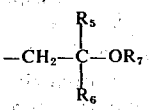

where each of $R_5$, $R_6$ and $R_7$ is hydrogen are prepared by reduction with an alkali metal aluminum hydride of the corresponding compounds where Z is —$CH_2COR_5$, where $R_5$ is hydrogen. The reduction is carried out in an inert organic solvent such as dioxane, tetrahydrofuran or diethyl ether at temperatures in the range from about 0° to 100°C.

The compounds of formula I where Z is

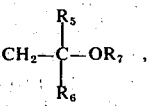

$R_5$ and $R_6$ are lower-alkyl, phenyl or phenyl-lower-alkyl, and $R_7$ is hydrogen are prepared by reaction of the corresponding compounds where Z is —$CH_2COR_5$, where $R_5$ is lower-alkyl, phenyl or phenyl-lower-alkyl, with one molar equivalent of an appropriate organo lithium, $R_6Li$, where $R_6$ has the meanings given above. The reaction is carried out in an inert organic solvent such as benzene or toluene. In this manner compounds where $R_5$ and $R_6$ are either the same or different lower-alkyl, phenyl or phenyl-lower-alkyl groups can be prepared depending upon the identity of the $R_5$ group and the choice of the particular organo lithium.

The compounds of formula I where $R_7$ and $R_6$ are hydrogen and $R_5$ is lower-alkyl, phenyl or phenyl-lower-alkyl are prepared by reduction with an alkali metal borohydride of the corresponding compounds where Z is —$CH_2COR_5$ and $R_5$ is lower-alkyl, phenyl or phenyl-lower-alkyl. The reaction is carried out in an inert organic solvent, for example lower-alkanols, such as methanol, ethanol or isopropanol.

The compounds of formula I where Z is

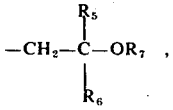

$R_5$ and $R_6$ are each hydrogen or the same or different lower-alkyl, phenyl or phenyl-lower-alkyl, and $R_7$ is lower-alkanoyl, benzoyl, or substituted-benzoyl are prepared by esterification of the corresponding compounds where $R_7$ is hydrogen, for example with an appropriate acid halide, anhydride or other acylating agent. The reaction is advantageously carried out using an appropriate acid halide in a pyridine solvent which serves as an acid acceptor to take up the hydrogen halide split out during the course of the reaction.

The compounds of formula I where $R_1$ is lower-alkenyl, lower-alkynyl or halo-lower-alkenyl are advantageously prepared from the corresponding compounds where $R_1$ is hydrogen by reaction of the latter with an appropriate lower-alkenyl halide, lower-alkynyl halide or halo-lower-alkenyl halide, as the case may be, in an inert organic solvent, for example a lower-alkanol, acetone or dimethylformamide (hereinafter designated DMF), in the presence of an acid-acceptor, for example an alkali metal carbonate or bicarbonate. A preferred solvent is DMF.

The compounds of formula I where $R_2$ and $R'_2$ is lower-alkanoyloxy are advantageously prepared from the corresponding compounds where $R_2$ and $R'_2$ is hydroxy by esterification with an appropriate lower-alkanoyl halide in the presence of pyridine.

The compounds of formula I where $R_2$ or $R'_2$ is amino are prepared by hydrolysis of the corresponding compounds where $R_2$ or $R'_2$ is lower-alkanoylamino or lower-alkoxycarbonylamino by heating the latter in aqueous alkali.

Alternatively, the compounds of formula I where $R_2$ or $R'_2$ is amino are prepared by reaction of the compounds of formula I where Z is $—CH_2COR_5$ and $R_1$ is hydrogen with nitric acid in glacial acetic acid. The reaction is carried out at temperatures from 0° to 5°C. The resulting nitro compound is then alkylated as desired in the manner described above to prepare compounds where $R_1$ has the other various meanings given above, and in a final step, the nitro group is reduced to the corresponding amino group by either catalytic means, for example with hydrogen over palladium-on-charcoal, or by chemical means, for example by iron and hydrochloric acid or by tin and hydrochloric acid.

As indicated in the reaction sequence shown above, the 7-$R_2$-8-$R'_2$-1$R_1$-2-Q-4a$\alpha$-$R_3$-5$\alpha$-$R_4$-1,2,3,4,4a,5,10,10a-octahydro-3,5-ethenobenzo[g]quinolines of formula IIIa where Q is $H_2$,

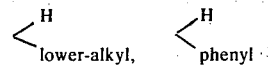

or

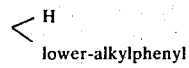

are produced along with the compounds of formula I (where Z is $—CH_2COR_5$) when the compounds of formula II where Y is $COR_5$ are heated with formic acid in an organic solvent or with a benzyl-di-lower-alkylammonium formate or a tri-lower-alkylammonium formate as described above. When the benzazocines of formula I are the desired product, it is preferred to carry out the reaction in mesitylene using a concentration of 0.05 molar in starting material of formula II and 1.0 molar in formic acid. This mixture gives a reaction temperature at reflux of about 120°C. and affords the benzazocines of formula I and the benzo[g]quinolines of formula IIIa in a ratio of from 2:1 to 3:1. By progressively decreasing the formic acid concentration, successively higher boiling mixtures are produced, which result in production of progressively increased relative amounts of the benzo[g]quinolines. Thus at formic acid concentrations of 0.5 molar and 0.15 molar (and 0.05 molar in starting material), the benzo[g]quinolines and benzazocines are produced in ratios of about 2:1 and 7:1, respectively. Similarly, by using a ratio of 1 mole of starting material to 5 moles of, respectively, benzyldimethylammonium formate or trimethylammonium formate or triethylammonium formate and heating the mixture (in the absence of any organic solvent) at 150°C. for about fifteen minutes, a mixture of benzo[g]quinoline and benzazocine is produced in ratios of 10:1, 3:1 and 20:1, respectively.

The two transformations thus take place simultaneously under the given conditions and are best seen by reference to the reaction sequence:

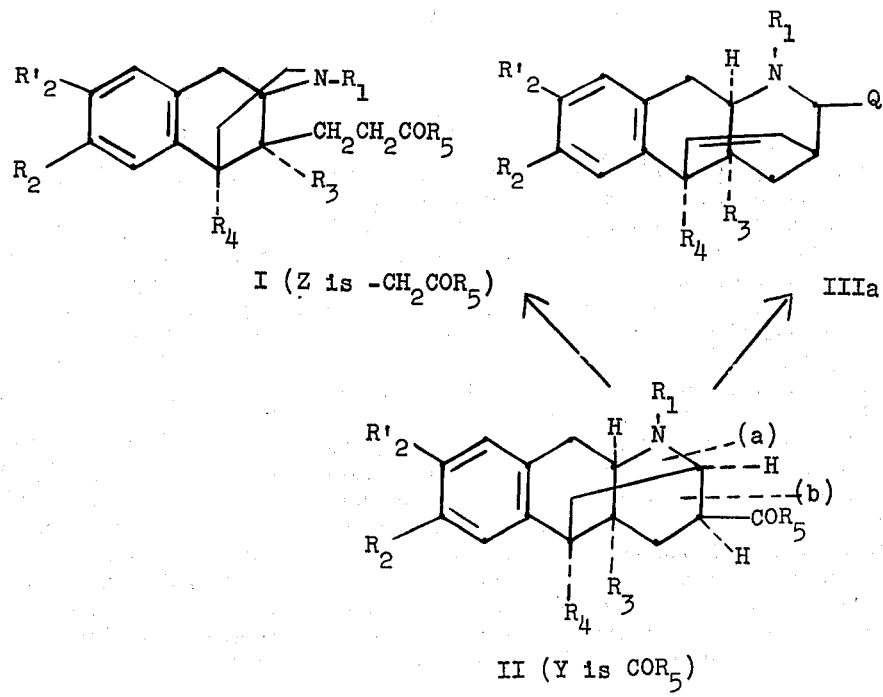

where $R_1$, $R_2$, $R'_2$, $R_3$, $R_4$, $R_5$ and Q have the meanings given above. It will be seen from the above that the compounds of formula I result by rupture, under the reaction conditions, of bond (b) in the compounds of formula II, whereas the compounds of formula IIIa result when bond (a) is broken, followed by ring closure between the nitrogen atom and the carbonyl group of the $COR_5$ moiety.

The compounds of formula IIIa where Q is oxo (=O), $R_1$ is hydrogen and $R_4$ is lower-alkyl are prepared by reaction of a 3-(4-$R_2$-3-$R'_2$-benzyl)-4-$R_3$-5-$R_4$-7-Y'-2-azabicyclo[2.2.2]oct-5-ene of formula IV where $R_1$ is hydrogen and Y' is $COOR_8$ with an alkali metal lower-alkoxide in a lower-alkanol solvent at a temperature in the range from 20° to 80°C. followed by heating the resulting 1-$R_3$-2-(4-$R_2$-3-$R'_2$-benzyl)-8-lower-alkylidene-3-azabicyclo[3.3.1]non-6-en-4-one of formula V with a mineral acid. The method is represented by the reaction sequence:

appropriate lower-alkyl, lower-alkenyl, lower-alkynyl, halo-lower-alkenyl, cycloalkyl, cycloalkyl-lower-alkyl, phenyl-lower-alkyl or substituted-phenyl-lower-alkyl ester of a strong mineral acid, such as esters of hydrochloric, hydrobromic or sulfuric acid. The reaction is preferably carried out in the presence of an acid-acceptor, for example an alkali metal carbonate or bicarbonate, and in an inert organic solvent such as methanol, ethanol, acetone, isopropanol and the like.

The 7-$R_2$-8-$R'_2$-1$R_1$-2-Q-4aα-$R_3$-5α-$R_4$-1,2,3,4,4a,5,10,10a-octahydro-3,5-ethanobenzo[g]quinolines of formula IIIb are prepared by catalytic reduction with hydrogen over a palladium-on-charcoal catalyst using an inert organic solvent, for example methanol, ethanol or isopropanol.

The 7-$R_2$-8-$R'_2$-1-$R_1$-3-Y-4aα-$R_3$-5α-$R_4$-1,2,3,4,4a,5,10,10a-octahydro-2,5-methanobenzo[g]quinolines of formula II which, as described above, serve as key intermediates for the preparation of the

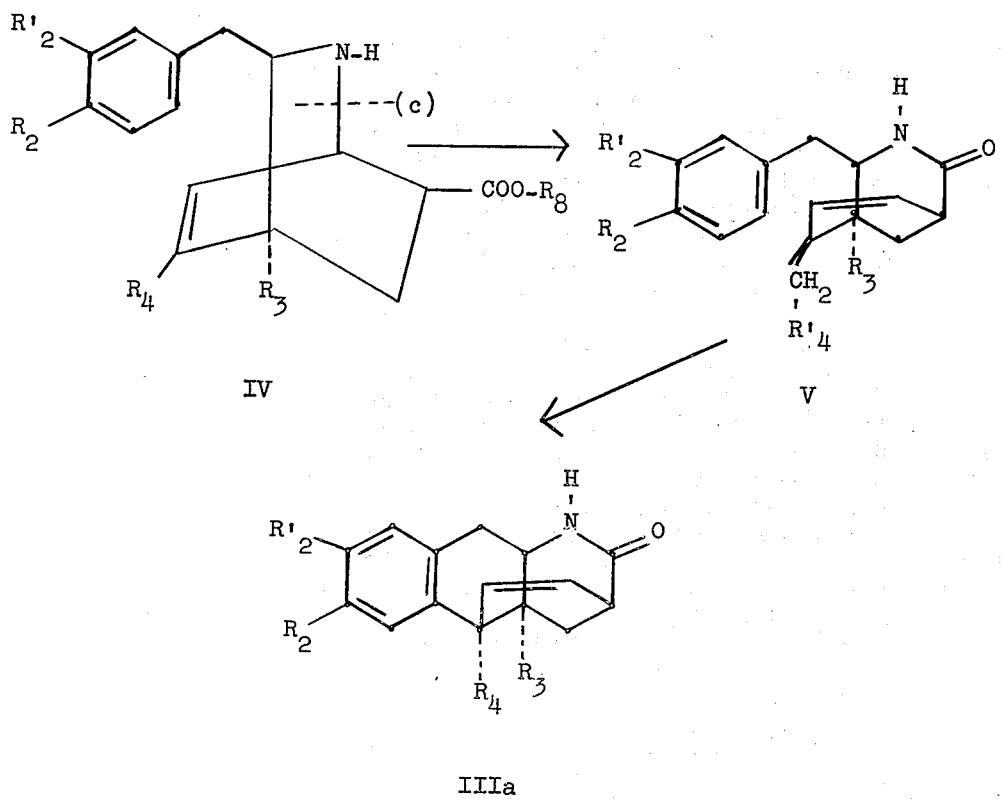

IV

V

IIIa

As indicated, the rearrangement of the compounds of formula IV to the compounds of formula V takes place by cleavage of the bond designated (c) in formula IV, cyclization of the ester group, $COOR_8$, to the nitrogen atom with formation of the lactam, shift of the endocyclic double bond and generation of an exocyclic double bond with loss of a proton from the $R_4$ lower-alkyl group.

The compounds of formula IIIa where Q is $H_2$ and $R_1$ is hydrogen are prepared by reduction of the corresponding compounds where Q is oxo (=O) with an alkali metal aluminum hydride. The reaction takes place in an organic solvent inert under the conditions of the reaction, for example diethyl ether, dibutyl ether, tetrahydrofuran, dioxane and the like, at a temperature in the range from 20°C. to 100°C.

The compounds of formula IIIa where $R_1$ is other than hydrogen are advantageously prepared by reaction of the compounds where $R_1$ is hydrogen with an final products of formulas I, IIIa and IIIb are in turn prepared as follows:

The compounds of formula II where Y is carboxy, cyano, carbo-lower-alkoxy, $COR_5$, COO-lower-alkylene-cycloalkyl or COO-lower-alkylene-phenyl are prepared by the acid catalyzed cyclization of an appropriate 2-$R_1$-3-(4-$R_2$-3-$R'_2$-benzyl)-4-$R_3$-5-$R_4$-7-Y'-2-azabicyclo[2.2.2.]oct-5-ene of formula IV. The reaction is carried out by adding the starting material of formula IV to the acid and either allowing the reaction mixture to stand at a temperature in the range from about 0°C. to about 10°C. or heating to about 100°C. Preferred acids are hydrofluoric acid, hydrobromic acid, sulfuric acid, phosphoric acid, and the like. A particularly preferred acid is hydrofluoric acid.

During the course of the cyclization reaction, various ester or ether groups, [e.g. compounds where Y' in the compounds of formula IV or Y in the compounds of formula II is an ester group or $R_2$ is, e.g. lower-alkoxy]

are often cleaved to the respective carboxylic acid or the phenolic compound, particularly when the reaction mixture is heated using, for example, hydrobromic acid. In such cases the products must be re-esterified or realkylated using standard procedures, if the esters or the ethers are the desired product. This difficulty is readily obviated by use of hydrofluoric acid as the acid catalyst which only requires a reaction temperature of around 0°–10°C. Under these mild conditions, ester and ether groups remain unchanged during the reaction.

The above described method for the preparation of compounds of formula II is particularly advantageous for the preparation of compounds of formula II where Y is carboxy, cyano, carbo-lower-alkoxy, $COR_5$, COO-lower-alkylene-cycloalkyl or COO—lower-alkylene-phenyl. The compounds of formula II where Y is the group

where $R_5$, $R_6$ and $R_7$ have the meanings given above are advantageously prepared from the compounds of formula II where Y has the other meanings given above by methods involving various transformations of the Y group as carboxy, carboxylic acid ester or $COR_5$ as described above in connection with the preparation of the compounds of formula I.

The compounds of formula II where Y is carboxy, cyano, carbo-lower-alkoxy, COO-lower-alkylene-cycloalkyl, COO-lower-alkylene-phenyl, or a group of the formula:

where one or both of $R_5$ and $R_6$ is hydrogen or lower-alkyl, and $R_7$ has the same meanings as in formula I can be converted to the compounds of formula II where Y is a $COR_5$ group by simple chemical transformations such as hydrolysis of a nitrile or ester to the carboxylic acid, or saponification of an ester of an hydroxymethyl-bearing compound ($R_5$, $R_6$ and $R_7$ are hydrogen) and oxidation of the hydroxymethyl group to the carboxylic acid, which can then be reacted with two moles of an appropriate organo lithium, $R_5Li$, to produce the compounds where Y is $COR_5$. Compounds of formula II where $R_7$ and one of $R_5$ and $R_6$ is hydrogen and the other is lower-alkyl, phenyl or phenyl-lower-alkyl can likewise be converted to the compounds where Y is $COR_5$ by oxidation. The compounds of formula II where Y has the above-indicated meanings are thus also useful as intermediates for preparing the compounds of formula II where Y is $COR_5$, which in turn are useful as intermediates for the preparation of the compounds of formula I.

The compounds of formula II where Y is the group

where $R_5$ and $R_6$ are hydrogen, lower-alkyl, phenyl or phenyl-lower-alkyl and $R_7$ is hydrogen, which as indicated above are intermediates for preparing the compounds of formula I, are prepared by saponification of the corresponding compounds where $R_7$ is lower-alkanoyl, benzoyl or substituted-benzoyl. The compounds of formula II where $R_7$ is lower-alkanoyl, benzoyl or substituted-benzoyl are thus intermediates for the compounds where $R_7$ is hydrogen. The ester forms are useful compounds for purification of the carbinols and serve as intermediates for the latter.

The compounds of formula II where $R_1$ is benzyl can be catalytically debenzylated to give the corresponding compounds where $R_1$ is hydrogen. The latter can then be realkylated with an appropriate alkylating agent to give other different compounds where $R_1$ has the meanings given above. Reduction is carried out in an inert organic solvent, for example ethanol, isopropanol, and the like, and at pressures from 40 to 100 pounds p.s.i. A preferred catalyst is palladium-on-charcoal. The alkylation of the compounds of formula II where $R_1$ is hydrogen is carried out in an inert organic solvent, for example acetone, ethanol or DMF, and in the presence of an acid-acceptor, for example alkali metal carbonates or bicarbonates.

Finally the 2-$R_1$-3-(4-$R_2$-3-$R'_2$-benzyl)-4-$R_3$-5-$R_4$-7-$Y'$-2-azabicyclo[2.2.2]oct-5-enes of formula IV, which serve as intermediates for the preparation of the key intermediates of formula II are themselves prepared by reaction of a Grignard reagent derived from a 4-$R_2$-3-$R'_2$-benzyl halide of formula VI with an appropriate 3-$R_3$-4-$R_4$-1-$R_1$-pyridinium halide of formula VII followed by Diels-Alder condensation of the resulting 2-(4-$R_2$-3-$R'_2$-benzyl)-3-$R_3$-4-$R_4$-1,2-dihydropyridine of formula VIII with an appropriate dienophile, $CH_2=CHY'$.

The reaction with the Grignard reagent is carried out at a temperature in the range from 0° to 25°C. in an inert organic solvent, for example diethyl ether, tetrahydrofuran or dibutyl ether and is effected by addition of a solution of the Grignard to a suspension of the quaternary salt in the reaction solvent. The resulting dihydro compound of formula VIII is generally not isolated and purified, but rather is carried forward directly to the next step involving reaction with the dienophile without further purification. The reaction of the dihydro compounds of formula VIII with the dienophile can either be carried out in an excess of the latter as a solvent or in an inert organic solvent such as benzene, toluene or xylene. Reaction is preferably carried out at the reflux temperature of the mixture.

The 3-$R_3$-4-$R_4$-pyridines, from which the quaternaries of formula VII are prepared, and also the 4-$R_2$-3-$R'_2$-benzyl halides, from which the Grignard reagents are prepared, are known classes of compounds.

Due to the presence of a basic amino grouping, the free base forms represented by formulas I, II, IIIa, IIIb and IV above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in stereochemically isomeric forms, that is, optical isomers and geometric isomers. If desired, the isolation or the production of a particular stereochemical form can be accomplished by application of the general principles known in the prior art. In the nomenclature employed for the compounds of formula I herein, "ax" stands for axial and "eq" for equatorial, and the configurations are given with reference to the hydroaromatic ring. Thus, the 6(eq), 11(ax) compounds of formula I are in the cis configuration, whereas the 6(eq), 11(eq) compounds are in the trans configuration.

In the nomenclature employed for the compounds of formulas II, IIIa and IIIb, again configuration are given with reference to the hydroaromatic ring, and the designation "β" indicates the cis configuration relative to the 2,5-methano bridge of the compounds of formula II or the 3,5-ethano (or 3,5-etheno) bridge of the compounds of formulas IIIa and IIIb. Conversely, the designation "α" indicates the trans configuration relative to the same groups.

In standard pharmacological test procedures, the compounds of formulas I, IIIa and IIIb and the acid-addition salts thereof have been found useful as depressants of the central nervous system, and more particularly have been found useful as analgesics and as antagonists of strong analgesics such as phenazocine, meperidine and morphine.

The compounds of formulas I, IIIa and IIIb can be administered in the same manner as known analgesics and antagonists of strong analgesics, i.e. parenterally or orally in any of the conventional pharmaceutical forms, as for instance solutions, suspensions, tablets, capsules, and the like.

As described above and as will be seen hereinbelow, many of the species of formulas I, II, IIIa, IIIb and IV are readily interconvertible by simple and well-known reactions such as reduction, oxidation, hydrolysis, esterification, etherification, and the like, so that they are also useful as intermediates for each other.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedures used to determine the analgesic and analgesic antagonist activities of the compounds of the invention have been described in detail in the prior art and are as follows: the acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319-323 (1966); the rat tail flick radiant thermal heat analgesic (agonist) test described by D'Amour and Smith, J. Pharmacol. Exptl. Therap. 72, 74 (1941 as modified by Bass and Vander-Brook, J. Am. Pharm. Assoc. Sci. Ed. 41, 569 (1956); and the phenazocine antagonist test, which is designed to measure the ability of a test agent to antagonize the effect of phenazocine in the aboveindicated rat tail flick response test, described by Harris and Pierson, J. Pharmacol. Exptl. Therap. 143, 141 (1964).

The structures of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventor or carrying out this invention, will now be described so as to enable any person skilled in the art to which it pertains to make and use the same. The melting points are uncorrected unless noted otherwise.

PREPARATION OF INTERMEDIATES
EXAMPLE 1

A solution of 76 g. (0.6 mole) of benzyl chloride in 450 ml. of diethyl ether was added to a mixture of 14.6 g. (0.6 moles) of magnesium turnings in 150 ml. of dry ether at such a rate as to maintain gentle reflux. The resulting solution was then added by filtration through glass wool to a suspension of 75 g. (0.3 mole) of 4-ethylpyridine methiodide in 150 ml. of ether. The mixture was stirred for three hours at room temperature, poured into a mixture of ice/water containing ammonium chloride, and the organic layer was separated, dried, filtered, and diluted with ether to a volume of 900 ml.

The solution containing 1-methyl-2-benzyl-4-ethyl-1,2-dihydropyridine was divided into three 300 ml. portions, and each portion was evaporated to dryness, dissolved, respectively, in 200 ml. portions of benzene, toluene and xylene, and the three separate solutions treated with 22 ml. of ethyl acrylate and refluxed overnight. The solutions were each allowed to cool, diluted with diethyl ether and extracted with 150 ml. of 1 N hydrochloric acid. The combined extracts were washed once with diethyl ether, then basified with 15 ml. of concentrated ammonium hydroxide and the mixtures each extracted with 150 ml. of diethyl ether. The extracts of the three samples afforded, respectively, 18.2 g., 20.0 g. and 19.3 g. of product as oils. The three samples were dissolved in diethyl ether and acidified with ethereal hydrochloric acid to give a total of 32.2 g. of ethyl 2-methyl-3-benzyl-5-ethyl-2-azabicyclo[2.2.2]oct-5-ene-7-carboxylate hydrochloride, m.p. 189°–191°C.

Following a procedure similar to that described in Example 1A, using either benzene, toluene or xylene as solvent, an appropriate 4-$R_2$-3-$R'_2$-benzylmagnesium chloride of formula VI, an appropriate 3-$R_3$-4-$R_4$-1-$R_1$-pyridinium halide of formula VII and an appropriate dienophile, $CH_2$=CHY', the following 2-$R_1$-3-(4-$R_2$-3-$R'_2$-benzyl)-4-$R_3$-5-$R_4$-7-Y'-2-azabicyclo[2.2.2]oct-5-enes of formula IV are prepared. Unless noted otherwise, the products were isolated and characterized in the form of the hydrochloride salt. The anion of the quaternary of formula VII is given in parentheses along with the weight of VII used.

Here and elsewhere throughout this specification in subsequent tables, the weights of starting materials (S.M.) and products (Prod.) are given in grams in the appropriate columns headed "Wt. ", and melting points of the final products, together with the solvent of recrystallization, are given in the last column.

Where weights of only one of several reactants are given, the weights of such other reactants can be calculated on a proportionate molar basis from the amounts used in the example referred to for the preparative procedure employed. In some instances, the products were neither characterized nor purified, either by distillation or recrystallization, but rather were used directly in the next step as isolated from the reaction mixture.

The particular form of the starting material or product, whether base or salt, is specified along with the weights by use of designations such as "base", "HCl", "HBr", etc. to indicate that the weights are given, respectively, for the free base or the hydrochloride, hydrobromide, etc. salts.

EXAMPLE 1Z

A solution of 21.1 g. (0.05 mole) of the ethyl 2,3-dibenzyl-5-ethyl-2-azabicyclo[2.2.2]oct-5-ene-7-carboxylate hydrochloride described above in Example 1B was dissolved in a solution of 100 ml. of 1N sodium hydroxide and 100 ml. of ethanol, and the solution was heated and stirred under reflux for four hours. The ethanol was then removed in vacuo, the mixture diluted with water and then acidified with glacial acetic acid. Extraction of the mixture with chloroform afforded 21.1 g. of a gummy material which was dissolved in methanol and treated with an excess of methanesulfonic acid. The solid which separated on dilution with diethyl ether was collected to give 15.1 g. of 2,3-dibenzyl-5-ethyl-2-azabicyclo[2.2.2]oct-5-ene-7-carboxylic acid methanesulfonate, m.p. 220°–222°C.

Table 1a

| Example | $R_1$/Y' | $R_2$/$R'_2$ | $R_3$/$R_4$ | Wt.VII/Wt.IV | m.p. (°C.)/Sol. |
|---|---|---|---|---|---|
| 1B | $C_6H_5CH_2$ | H | H | 23.4 (Cl⁻) | 196–199 |
|    | $COOC_2H_5$ | H | $C_2H_5$ | 15.3 | ethanol/ether |
| 1C | $C_6H_5CH_2$ | $CH_3O$ | H | 117 (Cl⁻) | 183–186 |
|    | $COOC_2H_5$ | H | $C_2H_5$ | 76 | ethanol/ether |
| 1D | $CH_3$ | $CH_3O$ | H | 124 (I⁻) | 202–204 |
|    | $COOC_2H_5$ | H | $C_2H_5$ | 76 | ethanol/ether |
| 1E | $CH_3$ | H | H | 117 (I⁻) | 237–238 |
|    | $COOC_2H_5$ | H | $CH_3$ | 57 | ethanol/ether |
| 1F | $C_6H_5CH_2$ | H | H | 109.9 (Cl⁻) | 215–217 |
|    | $COOC_2H_5$ | H | $CH_3$ | 114.9 | ethanol/ether |
| 1G | $C_6H_5CH_2$ | H | H | 117 (Cl⁻) | 106–111 (a) |
|    | $COCH_3$ | H | $C_2H_5$ | 43.7 | ethanol |
| 1H | $C_6H_5CH_2$ | $CH_3O$ | H | 154 (Cl⁻) | 216–219 |
|    | $COOC_2H_5$ | H | $CH_3$ | 120 | ethanol/ether |
| 1J | $CH_3$ | H | $CH_3$ | 75.9 (I⁻) | 168–170 |
|    | $COCH_3$ | H | $C_2H_5$ | 26.8 | ethanol/ether |
| 1K | $CH_3$ | H | $CH_3$ | 50 (I⁻) | 174 |
|    | $COCH_3$ | H | $CH_3$ | 19.3 | ethanol/ether |
| 1L | $CH_3$ | H | $CH_3$ | 37.4 (I⁻) | 240–241 (b) |
|    | CN | H | $CH_3$ | 17 | ethanol |
| 1M | $CH_3$ | $CH_3O$ | H | 165 (I⁻) | 200–202 (c) |
|    | $COOCH_3$ | H | $CH_3$ | 58.8 | ethanol/aceton |
| 1N | $C_6H_5CH_2$ | H | H | 165 (Cl⁻) | 165–170 (d) |
|    | $COCH_3$ | H | $CH_3$ | 123.1 | ethanol/ether |
| 1P | $CH_3$ | H | H | 27.9 (I⁻) | 146–149 |
|    | $COOC_2H_5$ | H | $CH_3OCH_2CH_2$ | 6.4 | ethanol/ether |
| 1Q | $C_3H_5$—$CH_2$ (e) | H | H | 11.6 (Br⁻) | 230 |
|    | $COOC_2H_5$ | H | $CH_3$ | 8.6 | ethanol |
| 1R | $CH_3$ | H | H | 184 (I⁻) | 171–174 |
|    | $COOC_2H_5$ | H | $C_3H_7$ | 71.3 | ethanol/ether |
| 1S | $C_6H_5CH_2$ | $CH_3O$ | H | 112 (Cl⁻) | 125–130 |
|    | $COCH_3$ | H | $CH_3$ | 64.5 | ethanol/ether |
| 1T | $C_6H_5CH_2$ | H | $CH_3$ | 11.7 (Cl⁻) | 218–220 |
|    | $COOC_2H_5$ | H | $CH_3$ | 6.1 | ethanol/ether |
| 1U | $C_6H_5CH_2$ | $CH_3O$ | $CH_3$ | 157 (Cl⁻) | 146 |
|    | $COCH_3$ | H | $CH_3$ | 15.3 | ethanol/ether |
| 1V | $C_6H_5CH_2$ | $CH_3O$ | H | 165 (Cl⁻) | 122–127 |
|    | $COCH_3$ | H | $C_2H_5$ | 105.3 | acetone |
| 1W | $C_6H_5CH_2$ | H | $CH_3$ | 238 (I⁻) | 166–168 |
|    | $COCH_3$ | H | $C_2H_5$ | 36.3 | ethanol/ether |
| 1X | $C_6H_5CH_2$ | H | $CH_3$ | 46.8 (Cl⁻) | oil |
|    | $COCH_3$ | H | $CH_3$ | 54 |  |
| 1Y | $CH_3$ | H | H | 40.0 (I⁻) | 127–129 (f) |
|    | $COOC_2H_5$ | H | $CH_2CH_2SC_6H_5$ | acetone |  |

(a) Free base
(b) Hydrochloride hemiethanolate
(c) The corresponding ethyl ester hydrochloride prepared similarly using ethyl acrylate as the dienophile has m.p. 205°–206°C. (from ethanol).
(d) The free base has m.p. 118°–120° (from isopropanol).
(e) Cyclopropylmethyl
(f) Oxalate

EXAMPLE 1AA

A solution of 10 g. (0.02 mole) of ethyl 2-benzyl-3-(4-methoxybenzyl)-5-methyl-2-azabicyclo[2.2.2]oct-5-ene-7-carboxylate hydrochloride described above in Example 1H in 100 ml. of absolute ethanol was reduced with hydrogen over 1.0 g. of 10% palladium-on-charcoal, and when reduction was complete, the catalyst was removed by filtration and the filtrate taken to dryness. The residue was recrystallized from ethanol/ether to give 7.0 g. of ethyl 3-(4-methoxybenzyl)-5-methyl-2-azabicyclo[2.2.2]oct-5-ene-7-carboxylate hydrochloride, m.p. 173°–175°C., which on further recrystallization gave material having m.p. 177°–179°C.

EXAMPLE 1BB

Following a procedure similar to that described in Example 1AA above, 42.6 g. (0.1 mole) of ethyl 2,3-dibenzyl-4,5-dimethyl-2-azabicyclo[2.2.2]oct-5-ene-7-carboxylate hydrochloride described in Example 1T above was reduced with hydrogen over palladium-on-charcoal and the product isolated as the hydrochloride salt to give 24.2 g. of ethyl 3-benzyl-4,5-dimethyl-2-azabicyclo[2.2.2]oct-5-ene-7-carboxylate hydrochloride, m.p. 223°–226°C. (from ethanol/ether).

Following a procedure similar to that described in Example 1A, using an appropriate 4-$R_2$-3-$R'_2$-benzylmagnesium chloride of formula VI, an appropriate 3-$R_3$-4-$R_4$-$R_4$-1-$R_1$-pyridinium halide of formula VII and methyl vinyl ketone as dienophile, the following 2-$R_1$-3-(4-$R_2$-3-$R'_2$-benzyl)-4-$R_3$-5-$R_4$-7-$CH_3CO$-2-azabicyclo[2.2.2]oct-5-enes of formula IV are prepared.

Table 1b

| Example | $R_1$ | $R_2/R'_2$ | $R_3/R_4$ |
|---|---|---|---|
| 1CC | $CH_3$ | H / Cl | H / $CH_3$ |
| 1DD | $CH_3$ | H / Br | H / $CH_3$ |
| 1EE | $CH_3$ | H / F | H / $CH_3$ |
| 1FF | $CH_3$ | H / $CF_3$ | H / $CH_3$ |
| 1GG | $CH_3$ | H / $CH_3$ | H / $CH_3$ |
| 1HH | $CH_3$ | $C_6H_5$ / H | H / $CH_3$ |
| 1JJ | $CH_3$ | $CH_2$<O,O | H / $CH_3$ |
| 1KK | $CH_3$ | H / H | H / H |
| 1LL | $CH_3$ | H / H | H / $ClCH_2CH_2$ |
| 1MM | $CH_3$ | H / H | |

Table 1b-continued

| Example | $R_1$ | $R_2/R'_2$ | $R_3/R_4$ |
|---|---|---|---|
| 1NN | $CH_3$ | H / H | $(CH_2)_3$< |
| | | | $(CH_2)_4$< |
| 1PP | $C_6H_{11}$ | $CH_3S$ / H | H / $CH_3$ |
| 1QQ | 4-$BrC_6H_4CH_2CH_2$ | $CH_3O$ / H | H / $CH_3$ |
| 1RR | 4-$ClC_6H_4CH_2CH_2$ | $CH_3CONH$ / H | H / $CH_3$ |
| 1SS | 4-$FC_6H_4CH_2CH_2$ | $C_2H_5OCONH$ / H | H / $CH_3$ |
| 1TT | 4-Cl-3-$CH_3C_6H_3CH_2CH_2$ | H / H | H / $CH_3$ |
| 1UU | 3-$CH_3COOC_6H_4CH_2CH_2$ | H / H | H / $CH_3$ |
| 1VV | 3,4-$(CH_3O)_2C_6H_3CH_2CH_2$ | H / H | H / $CH_3$ |
| 1WW | 4-$CH_3SC_6H_4CH_2CH_2$ | H / H | H / $CH_3$ |
| 1XX | 3-$CF_3C_6H_4CH_2CH_2$ | H / H | H / $CH_3$ |
| 1YY | 3-$CH_3CONHC_6H_4CH_2CH_2$ | H / H | H / $CH_3$ |
| 1ZZ | 3,4-$OCH_2OC_6H_3CH_2CH_2$ | H / H | H / $CH_3$ |
| 1AB | $CH_3$ | H / H | H / $CH_2CH_2SCH_3$ |

EXAMPLE 2

A. A mixture of 12.3 g. ((0.035 mole) of the ethyl 2-methyl-3-benzyl-5-ethyl-2-azabicyclo[2.2.2]oct-5-ene-7-carboxylate hydrochloride, described above in Example 1A, in 125 ml. of 48% aqueous hydrobromic acid was stirred under reflux for twenty-four hours and cooled. The solid which separated was collected to give 8.4 g. of 1-methyl-5α-ethyl-1,2,3,4,4a,5,10,10a-octahydro-2,5-methanobenzo[g]quinoline-3β-carboxylic acid hydrobromide, m.p. 290°–293°C., which on recrystallization from water gave material having m.p. 295°–299°C.

Following a procedure similar to that described in Example 2A, using an appropriate 2-$R_1$-3-(4-$R_2$-3-$R'_2$-benzyl)-4-$R_3$-5-$R_4$-7-$Y'$-2-azabicyclo[2.2.2]oct-5-ene of formula IV, the following 7-$R_2$-8-$R'_2$-1-$R_1$-3-Y-4aα-$R_3$-5α-$R_4$-1,2,3,4,4a,5,10,10a-octahydro-2,5-methanobenzo[g]quinolines of formula II are prepared. The cyclization can be carried out using hydrofluoric acid at 0°–15°C., concentrated sulfuric acid at ambient temperature, or hydrobromic acid in glacial acetic acid at reflux temperature. The particular acid used to promote reaction in each case is identified below by the designations HF, $H_2SO_4$ and HBr, as the case may be. Unless noted otherwise the products were isolated as the hydrochloride salts.

Table 2a

| Example | $R_1$/Y | $R_2/R'_2$ | $R_3/R_4$ | Wt.IV/Wt.II | m.p. (°C.)/Solv. |
|---|---|---|---|---|---|
| 2B | $C_6H_5CH_2$ | H | H | 42.6 | 258–260 |
| HBr | COOH (a) | H | $C_2H_5$ | 11.5 | ethanol/ether |
| 2C | $CH_3$ | HO | H | 58.1 | 293 (c) |
| HBr | COOH (b) | H | $C_2H_5$ | 30.2 | $H_2O$ |
| 2D | $CH_3$ | H | H | 50 | 269 (c) |
| HBr | COOH (a) | H | $CH_3$ | 36.7 | ethanol/ether |
| 2E | $C_6H_5CH_2$ | H | H | 10 | 109–111 (d) |
| $H_2SO_4$ | $COCH_3$ | H | $C_2H_5$ | 7.1 | methanol |
| 2F | $C_6H_5CH_2$ | $CH_3O$ | H | 10 | 225–228 |
| HF | $COOC_2H_5$ | H | $CH_3$ | 7.3 | acetone |
| 2G | $CH_3$ | H | $CH_3$ | 10 | 99–103 (d) |
| $H_2SO_4$ | $COCH_3$ | H | $C_2H_5$ | 3.7 | hexane |
| 2H | $CH_3$ | HO (e) | H | 45.0 | 283–284 |
| HBr | $COOCH_3$ | H | $CH_3$ | 17.6 | ethanol |
| 2J | $CH_3$ | H | H | 88.4 | 228–229 |
| HBr | $COOC_2H_5$ | H | $C_3H_7$ | 23.3 | isopropanol |

Table 2a-continued

| Example | $R_1$/Y | $R_2/R'_2$ | $R_3/R_4$ | Wt.IV/Wt.II | m.p. (°C.)/Solv. |
|---|---|---|---|---|---|
| 2K | $C_6H_5CH_2$ | $CH_3O$ | H | 5.0 | 126–129 (d) |
| HF | $COCH_3$ | H | $CH_3$ | 2.6 | ethanol |
| 2L | $C_6H_5CH_2$ | $CH_3O$ | H | 176 | 88–90 (d) |
| HF | $COCH_3$ | H | $C_2H_5$ | 43.2 | ethanol |
| 2M | $CH_3$ | $CH_3O$ | H | 153.7 | 101–102 (d) |
| HF | $COOC_2H_5$ | H | $CH_3$ | 94.6 | ethyl acetate |
| 2N | $C_6H_5CH_2$ | H | $CH_3$ | 200 | 207–209 |
| HF | $COOC_2H_5$ | H | $CH_3$ | 167 | ethanol/ether |
| 2P | $C_6H_5CH_2$ | $CH_3O$ | $CH_3$ | 4.3 | 125–126 (d) |
| HF | $COCH_3$ | H | $CH_3$ | 3.2 | ethanol |
| 2Q | $C_6H_5CH_2$ | H | $CH_3$ | 79.2 | 95–98 (d) |
| HF | $COCH_3$ | H | $C_2H_5$ | 29.3 | ethanol |
| 2R | $C_6H_5CH_2$ | $CH_3O$ | H | 0.5 | 244–246 |
| HF | $COOC_2H_5$ | H | $C_2H_5$ | 0.25 | ethanol/ether |
| 2S | $C_6H_5CH_2$ | H | H | 66 | 200–203 |
| HF | $COOC_2H_5$ | H | $CH_3$ | 53 | ethanol/ether |
| 2T | $C_6H_5CH_2$ | H | H | 10 | 136–138 (d) |
| $H_2SO_4$ | $COCH_3$ | H | $CH_3$ | 3 | ethanol |
| 2U | $CH_3$ | H | H | 1.0 | 189–191 |
| HF | $COOC_2H_5$ | H | $CH_2CH_2OCH_3$ | 0.85 | ethanol/ether |
| 2V | $CH_3$ | H | H | 10 | 185–189 |
| HF | $COOC_2H_5$ | H | $CH_2CH_2H_5$ | 5.6 | acetone |

(a) Starting material was the ethyl ester.
(b) Starting material was the methoxy ether/ethyl ester.
(c) Hydrobromide salt
(d) Free base
(e) Starting material was the methoxy ether/methyl ester.

EXAMPLE 2W

A solution of 4.2 g (0.01 mole) of ethyl 1-methyl-5α-[2-(phenylthio)ethyl]-1,2,3,4,4a, 5,10,10a-octahydro-2,5-methanobenzo[g]quinoline-3β-carboxylate described in Example 2V in 80 ml. of glacial acetic acid was treated with 1.4 ml. of 30% aqueous hydrogen peroxide, allowed to stand at ambient temperature for one hour and fifteen minutes and then concentrated to dryness in vacuo at 40°C. The residue was partitioned between dilute sodium hydroxide and methylene dichloride and the organic layer separated, dried and taken to dryness to give 5.0 g. of ethyl 1-methyl-5α-[2-(phenylsulfinyl)ethyl]-1,2,3,4,4a,5,10,10a-ooctahydro-2,5-methanobenzo[g]guinoline-3β-carboxylate as an oil.

The latter (14.0 g., 0.032 mole) was distilled under reduced pressure, and the fraction boiling at 122°–156°C./0.03–0.11 mm. was collected (7 g.) and chromatographed on silica in a 6:4 solution of hexane:ether. The column was eluted until the yellow color passed through, and the next 550 ml. was collected separately and taken to dryness to give 6.4 g. of a gum which was dissolved in anhydrous ether and diluted with ethereal hydrogen chloride. The solid which separated was collected and dried to give 3.8 g of ethyl 1-methyl-5α-vinyl-1,2,3,4,4a,5,10,10a-octahydro-2,5-methanobenzo[g]quinoline-3β-carboxylate hydrochloride, m.p. 241°–242°C.

The latter (2.1 g., 0.006 mole) was converted to the free base, and the base in 15 ml. of tetrahydrofuran was treated with 15.6 ml. of a 1M solution of diborane in tetrahydrofuran. The solution was stirred for an hour and a half, poured into 10 ml. of ice water, the mixture basified with 3.6 ml. of 3N sodium hydroxide, treated with 2.2 ml. of 30% hydrogen peroxide. After stirring for an hour, the mixture was filtered, diluted with water, extracted with ether and the ether extracts extracted with dilute hydrochloric acid. Isolation of the basic product from the aqueous acid medium in the usual manner by basifying and extraction with ether and conversion of the product to the hydrochloride salt gave ethyl 1-methyl-5α-(2-hydroxyethyl)-1,2,3,4,4a,5,10,10a-octahydro-2,5-methanobenzo[g-]quinoline-3β-carboxylate hydrochloride, m.p. 212°–216°C. (from acetone).

Following a procedure similar to that described in Example 2A, using an appropriate 2-$R_1$-3-(4-$R_2$-3-$R'_2$-benzyl)-4-$R_3$-5-$R_4$-7-$Y'$-2-azabicyclo[2.2.2]oct-5-ene of formula IV and hydrofluoric acid at 0°–15°C., the following 7-$R_2$-8-$R'_2$-1-$R_1$-3-Y-4aα-$R_3$-5α-$R_4$-1,2,3,4,4a,5,10,10a-octahydro-2,5methanobenzo[g]quinolines of formula II are prepared.

Table 2b

| Example | $R_1$/Y | $R_2/R'_2$ | $R_3/R_4$ |
|---|---|---|---|
| 2X | $C_6H_5CH_2$ | $CH_3O$ | H |
|  | $COOC_2H_5$ | H | $CH_3$ |
| 2Y | $CH_3$ | H | $CH_3$ |
|  | $COCH_3$ | H | $CH_3$ |
| 2Z | $CH_3$ | H | $CH_3$ |
|  | CN | H | $CH_3$ |
| 2AA | cyclopropyl-$CH_2$ | H | H |
|  | $COOC_2H_5$ | H | $CH_3$ |
| 2BB | $CH_3$ | H | H |
|  | $COCH_3$ | Cl | $CH_3$ |
| 2CC | $CH_3$ | H | H |
|  | $COCH_3$ | Br | $CH_3$ |
| 2DD | $CH_3$ | H | H |
|  | $COCH_3$ | F | $CH_3$ |
| 2EE | $CH_3$ | H | H |
|  | $COCH_3$ | $CF_3$ | $CH_3$ |
| 2FF | $CH_3$ | H | H |
|  | $COCH_3$ | $CH_3$ | $CH_3$ |
| 2GG | $CH_3$ | $C_6H_5$ | H |
|  | $COCH_3$ | H | $CH_3$ |
| 2HH | $CH_3$ | $CH_2{<}^O_O$ | H |
|  | $COCH_3$ |  | $CH_3$ |
| 2JJ | $CH_3$ | H | H |
|  | $COCH_3$ | H | H |
| 2KK | $CH_3$ | H | H |
|  | $COCH_3$ | H | $ClCH_2CH_2$ |
| 2LL | $CH_3$ | H | H |
|  | $COCH_3$ | H | $(CH_2)_3{<}$ |
| 2MM | $CH_3$ | H | H |
|  | $COCH_3$ | H | $(CH_2)_4{<}$ |
| 2NN | $C_6H_{11}$ | $CH_3S$ | H |
|  | $COCH_3$ | H | $CH_3$ |
| 2PP | 4-$BrC_6H_4CH_2CH_2$ | $CH_3O$ | H |
|  | $COCH_3$ | H | $CH_3$ |
| 2QQ | 4-$ClC_6H_4CH_2CH_2$ | $CH_3CONH$ | H |
|  | $COCH_3$ | H | $CH_3$ |
| 2RR | 4-$FC_6H_4CH_2CH_2$ | $C_2H_5OCONH$ | H |
|  | $COCH_3$ | H | $CH_3$ |
| 2SS | 4-Cl-3-$CH_3C_6H_3CH_2CH_2$ | H | H |
|  | $COCH_3$ | H | $CH_3$ |
| 2TT | 3-$CH_3COOC_6H_4CH_2CH_2$ | H | H |
|  | $COCH_3$ | H | $CH_3$ |

Table 2b-continued

| Example | $R_1$/Y | $R_2$/$R'_2$ | $R_3$/$R_4$ |
|---|---|---|---|
| 2UU | 3,4-$(CH_3O)_2C_6H_3CH_2CH_2$<br>$COCH_3$ | H<br>H | H<br>$CH_3$ |
| 2VV | 4-$CH_3SC_6H_4CH_2CH_2$<br>$COCH_3$ | H<br>H | H<br>$CH_3$ |
| 2WW | 3-$CF_3C_6H_4CH_2CH_2$<br>$COCH_3$ | H<br>H | H<br>$CH_3$ |
| 2XX | 3-$CH_3CONHC_6H_4CH_2CH_2$<br>$COCH_3$ | H<br>H | H<br>$CH_3$ |
| 2YY | 3,4-$OCH_2OC_6H_3CH_2CH_2$<br>$COCH_3$ | H<br>H | H<br>$CH_3$ |
| 2ZZ | $CH_3$<br>$COCH_3$ | H<br>H | H<br>$CH_2CH_2SCH_3$ |

EXAMPLE 3

A solution containing 21.3 g. (0.05 mole) of ethyl 2,3-dibenzyl-5-ethyl-2-azabicyclo[2.2.2]oct-5-ene-7-carboxylate hydrochloride (described in Example 1B) in 200 ml. of ethanol was reduced over 2.1 g. of palladium-on-charcoal using the procedure described above in Example 1AA. There was thus obtained 18 g. of ethyl 3-benzyl-5-ethyl-2-azabicyclo[2.2.2]oct-5-ene-7-carboxylate hydrochloride, without further purification, was dissolved in 170 ml. of 48% hydrobromic acid and heated under reflux for about eight hours. The crude product obtained was recrystallized from water to give 9.4 g. of 5α-ethyl-1,2,3,4,4a,5,10,10a-octahydro-2,5-methanobenzo[g]quinoline-3β-carboxylic acid hydrobromide, m.p.> 310°C.

EXAMPLE 4

A. A mixture of 48.3 g. (0.13 mole) of 1-methyl-5α-ethyl-1,2,3,4,4a,5,10,10a-octahydro-2,5-methanobenzo[g]quinoline-3β-carboxylic acid hydrobromide (described in Example 2A) in 480 ml. of absolute ethanol was treated with anhydrous hydrogen chloride until all material has dissolved. The solution was refluxed for three hours, taken to dryness, and the solid residue was partitioned between dilute ammonium hydroxide and diethyl ether. The ether layer was separated, combined with additional ether washes of the aqueous layer, and the combined organic extracts dried and evaporated to dryness. The resulting solid residue was dissolved in ethanol and treated with ethereal hydrogen chloride to give 39.3 g. of ethyl 1-methyl-5α-ethyl-1,2,3,4,4a,5,10,10a-octahydro-2,5-methanobenzo[g-]quinoline-3β-carboxylate hydrochloride, m.p. 244°–246°C.

Following a procedure similar to that described in Example 4A, using an appropriate 7-$R_2$-8-$R'_2$-1-$R_1$-4aα-$R_3$-5α-$R_4$-1,2,3,4,4a,5,10,10a-octahydro-2,5-methanobenzo[g]quinoline-3-carboxylic acid hydrobromide of formula II and an appropriate loweralkanol, the corresponding lower-alkyl esters of formula II given in Table 4 below are prepared. Unless noted otherwise, melting points are given for the free base form.

Table 4

| Example | $R_1$/Y | $R_2$/$R'_2$ | $R_3$/$R_4$ | Wt.acid/Wt.Prod. | m.p. (°C.)/Solv. |
|---|---|---|---|---|---|
| 4B | $CH_3$<br>$COOCH_3$ | H<br>H | H<br>$CH_3$ | 10.3<br>5.0 | 129–133<br>methanol |
| 4C | H<br>$COOC_2H_5$ | H<br>H | H<br>$C_2H_5$ | 11.2<br>8.0 | 245–246 (a)<br>ethanol/ether |
| 4D | $CH_3$<br>$COOCH_3$ | HO<br>H | H<br>$C_2H_5$ | 10.0<br>5.4 | 190–193<br>ethyl acetate/hexane |

EXAMPLE 5

A solution of 53.7 g. (0.15 mole) of 1-benzyl-3β-acetyl-5α-methyl-7-methoxy-1,2,3,4,4a,5,10,10a-octahydro-2,5-methanobenzo[g]quinoline (described in Example 2K) in 250 ml. of 48% aqueous hydrobromic acid was warmed on a steam bath for two hours and then filtered and cooled. The solid which had precipitated was collected and recrystallized from water to give 10.3 g. of 1-benzyl-3β-acetyl-5α-methyl-7-hydroxy-1,2,3,4,4a,5,10,10a-octahydro-2,5-methanobenzo[g]quinoline hydrobromide, m.p. 192°–197°C.

EXAMPLE 6

A. A solution of 21.7 g. (0.06 mole) of 1-benzyl-3β-acetyl-5α-ethyl-1,2,3,4,4a,5,10,10a-octahydro-2,5-methanobenzo-[g]quinoline (described in Example 2E) in 100 ml. of ethanol was made acidic with aqueous hydrochloric acid, and the solution was reduced with hydrogen over 2.0 g. of 10% palladium-on-charcoal at room temperature using a Parr shaking apparatus. When reduction was complete, the catalyst was removed by filtration, the filtrate concentrated to dryness in vacuo, and the residue recrystallized from isopropanol to give 14.4 g. of 3β-acetyl-5α-ethyl-1,2,3,4,4a,5,10,10a-octahydro-2,5-methanobenzo[g]quinoline hydrochloride, m.p. 240°–241°C.

Following a procedure similar to that described in Example 6A, using an appropriate 7-$R_2$-8-$R'_2$-1benzyl-3-Y-4aα-$R_3$-5α-$R_4$-1,2,3,4,4a,5,10,10a-octahydro-2,5-methanobenzo[g]-quinoline of formula II, the corresponding debenzylated compounds of formula II in Table 6 below where $R_1$ in each case is hydrogen are prepared. The compound of Example 6B was prepared from, and isolated as, the hydrobromide salt, and the compound of Example 6C was prepared from, and isolated as, the hydrochloride salt.

Table 6

| Example | Y | $R_2$/$R'_2$ | $R_3$/$R_4$ | Wt.S.M./Wt.Prod. | m.p. (°C.)/Solv. |
|---|---|---|---|---|---|
| 6B | $COCH_3$ | HO<br>H | H<br>$CH_3$ | 8.2<br>4.8 | 247–248<br>acetonitrile |
| 6C | $COOC_2H_5$ | H<br>H | $CH_3$<br>$CH_3$ | 42.6<br>26.4 | 213–216<br>ethanol/ether |

EXAMPLE 7

A. A mixture of 5.0 g. (0.017 mole) of ethyl 5α-ethyl-1,2,3,4,4a,5,10,10a-octahydro-2,5-methanobenzo[g-]quinoline-3β-carboxylate hydrochloride (described in Example 4C), 2.8 g. (0.17 mole) of cyclopropylmethyl bromide and 1.4 g. (0.017 mole) of sodium bicarbonate in 40 ml. of DMF was stirred and refluxed for three hours, and then evaporated to dryness in vacuo. The residue was partitioned between water and diethyl ether, the ether layer was washed with water, dried, charcoaled and filtered, and the filtrate was diluted with ethanol and acidified with ethereal hydrogen chloride. The solid which separated was collected and recrystallized from ethanol/ether to give 4.4 g. of ethyl 1-cyclopropylmethyl-5α-ethyl-1,2,3,4,4a,5,10,10a-octahydro-2,5-methanobenzo[g]quinoline-3β-carboxylate hydrochloride, m.p. 215°–217°C.

B. Following a procedure similar to that described in Example 7A, 27.6 g. (0.091 mole) of 3β-acetyl-5α-ethyl-1,2,3,4,4a,5,10,10a-octahydro-2,5-methanobenzo[g]quinoline hydrochloride (described in Example 6A) was alkylated with 14.9 g. (0.11 mole) of cyclopropylmethyl bromide in the presence of sodium bicarbonate and the product converted to the hydrochloride salt to give 24.1 g. of 1-cyclopropylmethyl-3β-acetyl-5α-ethyl-1,2,3,4,4a,5,10,10a-octahydro-2,5methanobenzo[g]quinoline hydrochloride, which on recrystallization from ethanol/ether afforded material having m.p. 202°–204°C.

EXAMPLE 8

A. A mixture of 18.0 g. (0.05 mole) of 5α-ethyl-1,2,3,4,4a,5,10,10a-octahydro-2,5methanobenzo[g]quinoline-3β-carboxylic acid hydrobromide (described in Example 3), 20.4 g. (0.11 mole) of β-phenylethyl bromide and 13.5 g. (0.16 mole) of sodium bicarbonate in 200 ml. of DMF was stirred under reflux for four hours, and then worked up in the manner described above in Example 7A. The crude product was converted to the hydrochloride salt which was recrystallized from isopropanol to give 4.4 g. of 2-phenylethyl 1-(2-phenylethyl)-5α-ethyl-1,2,3,4,4a,5,10,10a-octahydro-2,5-methanobenzo[g]quinoline-3β-carboxylate hydrochloride, m.p. 237°–238°C.

B. Following a procedure similar to that described in Example 8A, 20.5 g. (0.058 mole) of 5α-ethyl-1,2,3,4,4a,5,10,10a-octahydro-2,5-methanobenzo[g]quinoline-3β-carboxylic acid hydrobromide (described in Example 3) was reacted with 19.8 g. (0.12 mole) of cyclopropylmethyl bromide in the presence of sodium bicarbonate, and the product converted to the hydrochloride salt which was recrystallized from ethanol/ether to give 6.6 g. of cyclopropylmethyl 1-(cyclopropylmethyl)-5α-ethyl-1,2,3,4,4a,5,10,10a-octahydro-2,5-methanobenzo[g]quinoline-3β-carboxylate hydrochloride, m.p. 184°–187°C.

EXAMPLE 9

A. A solution of 0.035 mole of ethyl 1-methyl-5α-propyl-1,2,3,4,4a,5,10,10a-octahydro-2,5-methanobenzo[g]quinoline-3β-carboxylate (obtained from 14.4 g. of the corresponding hydrochloride described above in Example 2J) in diethyl ether was added in a fine stream to 81 ml. of a 2.16M solution (0.175 mole) of methyl lithium in diethyl ether. When addition was complete, the mixture was stirred for about 30 minutes, allowed to stand overnight, and then poured into an ice/aqueous ammonium chloride mixture. The ether layer was separated, the aqueous layer washed with diethyl ether, and the combined organic extracts washed with saturated brine, dried, filtered, and concentrated to dryness. The residue was dissolved in ethanol/ether, and the solution acidified with ethereal hydrogen chloride. The solid which separated was collected and recrystallized from ethanol/ether to give 2.5 g. of 1-methyl-3β-(2-hydroxy-2propyl)-5α-propyl-1,2,3,4,4a,5,10,10a-octahydro-2,5-methanobenzo[g]quinoline hydrochloride, m.p. 257°–258°C.

Following a procedure similar to that described in Example 9A, using an appropriate lower-alkyl 7-$R_2$-8-$R'_2$-1-$R_1$-4aα-$R_3$-5α-$R_4$-1,2,3,4,4a,5,10,10a-octahydro-2,5-methanobenzo[g]-quinoline-3-carboxylate of formula II described in Examples 4A, 4B, 4D, 8A, 2M and 7A, respectively, and methyl lithium, the following compounds of formula II in Table 9, where Y in each case is $C(CH_3)_2OH$, are prepared. In each case, the weights of starting materials are given for the free base form, and unless noted otherwise, melting points of the products are given for the hydrochloride salt.

Table 9

| Example | $R_1$ | $R_2/R'_2$ | $R_3/R_4$ | Wt.S.M./Wt.Prod. | m.p. (°C.)/Solv. |
|---|---|---|---|---|---|
| 9B | $CH_3$ | H | H | 15.7 | 275 |
|  |  | H | $C_2H_5$ | 6.9 | ethanol |
| 9C | $CH_3$ | H | H | 15 | 256–257 |
|  |  | H | $CH_3$ | 12.2 | ethanol/ether |
| 9D | $CH_3$ | HO | H | 12.9 | 272 |
|  |  | H | $C_2H_5$ | 8.1 | ethanol/ether |
| 9E | $C_6H_5CH_2CH_2$ | H | H | 8.2 | 248–248.5 |
|  |  | H | $C_2H_5$ | 3.9 | ethanol/ether |
| 9F | $CH_3$ | $CH_3O$ | H | 25 | 126–127 (a) |
|  |  | H | $CH_3$ | 22.1 | hexane |
| 9G | $C_3H_5$—$CH_2$ (b) | H | H | 6.1 | 256 |
|  |  | H | $C_2H_5$ | 4.5 | ethanol/ether |

(a) Free base
(b) Cyclopropylmethyl

EXAMPLE 10

A. To a suspension of 44.1 g. (0.16 mole) of 1-methyl-5α-ethyl-1,2,3,4,4a,5,10,10a-octahydro-2,5-methanobenzo[g]quinoline-3β-carboxylic acid (from the hydrobromide described in Example 2A) in 390 ml. of diethyl ether was added in a fine stream 230 ml. (0.5 mole) of a 2.16M solution of methyl lithium in diethyl ether. When addition was complete, the mixture was stirred for three hours, poured into an ice/aqueous ammonium chloride solution, and worked up in the manner described in Example 9A. There was thus obtained 32.8 g. of product as an oily crude base, 3.3 g. of which was converted to the hydrochloride salt. The latter was recrystallized from methanol/diethyl ether to give 2.3 g. of 1-methyl-3β-acetyl-5α-ethyl-1,2,3,4,4a,5,10,10a-octahydro-2,5-methanobenzo[g]-quinoline hydrochloride, m.p. 191°C.

Following a procedure similar to that described in Example 10A, using an appropriate 7-$R_2$-8-$R'_2$-1-$R_1$-

$4a\alpha$-$R_3$-$5\alpha$-$R_4$-1,2,3,4,4a,5,10,10a-octahydro-2,5methanobenzo[g]quinoline-3-carboxylic acid of formula II described in Examples 2A and 2C and an appropriate organo lithium, $R_5$Li, the following compounds of formula II in Table 10a are prepared. The form (acid or base) of the starting material is given in each case in parentheses along with the weight of starting material, and. of course, salt forms were converted to the free base before reaction with the organo lithium. The melting points for the compounds of Examples 10B and 10D are given for the hydrochloride salts and for the free base of the compound of Example 10C.

octahydro-2,5-methanobenzo[g]guinoline, m.p. 103°–105°C. (from hexane) (the hydrochloride salt shows m.p. 263°–265°C., from isopropanol/DMF), designated isomer B, was prepared in a similar fashion by reaction of 1-methyl-3$\beta$-butyryl-5$\alpha$-ethyl-1,2,3,4,4a,5,10,10a-octahydro-2,5methanobenzo[g-]quinoline (from the hydrochloride salt described in Example 10B) with methyl lithium.

Following a procedure similar to that described in Example 11A, using an appropriate 7-$R_2$-8-$R'_1$-1-$R_1$-3$\beta$-acetyl-4a$\alpha$-$R_3$-5$\alpha$-$R_4$-1,2,3,4,4a,5,10,10a-octahydro-2,5-methanobenzo[g]quinoline described in Ex- Table 10a

| Example | $R_1$/COR$_5$ | $R_2$/$R'_2$ | $R_3$/$R_4$ | Wt.S.M./Wt.Prod. | m.p. (°C.)/Solv. |
|---------|---------------|--------------|-------------|-------------------|-------------------|
| 10B | CH$_3$ | H | H | 12.1 (base) | 190–191 |
|  | COC$_3$H$_7$ | H | C$_2$H$_5$ | 8.0 | isopropanol/ether |
| 10C | CH$_3$ | HO | H | 36 (HBr) | 201–204 |
|  | COCH$_3$ | H | C$_2$H$_5$ | 18.9 | DMF/H$_2$O |
| 10D | CH$_3$ | H | H | 8.6 (base) | 200–202 |
|  | COC$_6$H$_5$ | H | C$_2$H$_5$ | 6.4 (HCl) | ethanol/ether |

Following a procedure similar to that described in Example 10A, using an appropriate 7-$R_2$-8-$R'_2$-1-$R_1$-4a$\alpha$-$R_3$-5$\alpha$-$R_4$-1,2,3,4,4a,5,10,10a-octahydro-2,5-methanobenzo[g]quinoline-3$\beta$-carboxylic acid (prepared by alkaline saponification of the corresponding esters described in Examples 2V and 2W) and methyl lithium, the following compounds of formula II in Table 10b are prepared where, in each instance, Y is COCH$_3$.

amples 2G and 2K, respectively, and methyl lithium, the following compounds of formula II in Table 11 are prepared, where in each instance Y is C(CH$_3$)$_2$OH. All melting points are for the hydrochloride salts.

Table 11

| Example | $R_1$ | $R_2$/$R'_2$ | $R_3$/$R_4$ | Wt.S.M./Wt.Prod. | m.p. (°C.)/Solv. |
|---------|-------|--------------|-------------|-------------------|-------------------|
| 11C | CH$_3$ | H | CH$_3$ | 5.0 (base) | 247–248 |
|  |  | H | C$_2$H$_5$ | 4.4 | ethanol/ether |
| 11D | C$_6$H$_5$CH$_2$ | CH$_3$O | H | 15.0 (base) | 236–237 |
|  |  | H | CH$_3$ | 12.2 | ethanol/ether |

Table 10b

| Example | $R_1$ | $R_2$/$R'_2$ | $R_3$/$R_4$ |
|---------|-------|--------------|-------------|
| 10E | CH$_3$ | H | H |
|  |  | H | CH$_2$CH$_2$SC$_6$H$_5$ |
| 10F | CH$_3$ | H | H |
|  |  | H | CH$_2$CH$_2$SOC$_6$H$_5$ |
| 10G | CH$_3$ | H | H |
|  |  | H | CH=CH$_2$ |
| 10H | CH$_3$ | H | H |
|  |  | H | CH$_2$CH$_2$OH |

EXAMPLE 11

A. A solution of 2.8 g. (0.01 mole) of 1-methyl-3$\beta$-acetyl-5$\alpha$-ethyl-1,2,3,4,4a,5,10,10a-octahydro-2,5-methanobenzo[g]quinoline (from the hydrochloride described in Example 10A) in 25 ml. of diethyl ether was added dropwise to a solution of 40 ml. (0.032 mole) of a 0.8M solution of propyl lithium in diethyl ether. When addition was complete, the mixture was allowed to stand for 1 hour, poured into an ice/aqueous ammonium chloride solution and worked up in the manner described in Example 9A. The product thus obtained was converted to the hydrochloride salt which was recrystallized from ethanol/ether to give 1.2 g. of 1-methyl-3$\beta$-(2-hydroxy-2-pentyl)-5$\alpha$-ethyl-1,2,3,4,4a,5,10,10a-octahydro-2,5-methanobenzo[g-]quinoline hydrochloride, m.p. 227°–230°C. (designated isomer A).

B. The isomeric compound, 1-methyl-3$\beta$-(2-hydroxy-2-pentyl)-5$\alpha$-ethyl-1,2,3,4,4a,5,10,10a-

EXAMPLE 12

A solution of 0.076 mole of ethyl 1-methyl-5$\alpha$-ethyl-1,2,3,4,4a,5,10,10a-octahydro-2,5-methanobenzo[g-]quinoline-3$\beta$-carboxylate (obtained from 26.7 g. of the hydrochloride salt described in Example 4A) in 250 ml. of anhydrous diethyl ether was added in a fine stream to a stirred suspension of 2.9 g. (0.076 mole) of lithium aluminum hydride in 125 ml. of diethyl ether. When addition was complete, the mixture was stirred for about one hour, treated dropwise with 5.8 ml. of water, stirred for an additional 10 minutes, and then filtered through filter aid. The filter cake was washed with several portions of diethyl ether, and the combined filtrates were evaporated to dryness to give 20.8 g. of the product in the form of the free base, 7.0 g. of which was dissolved in 35 ml. of ethanol and acidified with ethereal hydrogen chloride. The solid which separated was collected and recrystallized from ethanol/diethyl ether to give 7.6 g. of 1-methyl-3$\beta$-hydroxymethyl-5$\alpha$-ethyl- 1,2,3,4,4a,5,10,10a-octahydro-2,5-methanobenzo[g]quinoline hydrochloride, m.p. 273°–278°C.

EXAMPLE 13

A. A solution of 8.5 g. (0.03 mole) of 1-methyl-3$\beta$-acetyl-5$\alpha$-ethyl-1,2,3,4,4a,5,10,10a-octahydro-2,5-methanobenzo-[g]quinoline hydrochloride (described in Example 10A) in 135 ml. of ethanol was added in a fine stream to a solution of 1.2 g. (0.03 mole) of sodium borohydride in 25 ml. of ethanol. When addition was complete, the mixture was stirred for four and one half hours and then decanted from the precipitated solids. The liquid layer was evaporated to dryness, the residue dissolved in dilute hydrochloric acid and the solution basified with concentrated ammonium hydroxide. Extraction of the mixture with diethyl ether afforded 7.5 g. of crude base which was converted to the hydrochloride salt to give 3.3 g. of 1-methyl-3β-(1-hydroxyethyl)-5α-ethyl-1,2,3,4,4a,5,10,10a-octahydro-2,5-methanobenzo[g]quinoline hydrochloride, m.p. 305°–307°C.

B. Following a procedure similar to that described in Example 13A, 25.0 g. (0.076 mole) of ethyl 1-methyl-5α-methyl-7-methoxy-1,2,3,4,4a,5,10,10a-octahydro-2,5-methanobenzo[g]-quinoline-3β-carboxylate described in Example 2M was reduced with 2.9 g. (0.76 mole) of sodium borohydride in the presence of 6.6 g. (0.076 mole) of lithium bromide in 200 ml. of tetrahydrofuran, and the product converted to the hydrochloride salt to give 21.4 g. of 1-methyl-3β-hydroxymethyl-5α-methyl-7-methoxy-1,2,3,4,4a,5,10,10a-octahydro-2,5-methanobenzo[g]-quinoline hydrochloride, m.p. 264°–268°C. (from ethanol/ether).

EXAMPLE 14

A. A solution of 4.8 g. (0.018 mole) of 1-methyl-3β-hydroxymethyl-5α-ethyl-1,2,3,4,4a,5,10,10a-octahydro-2,5-methanobenzo[g]quinoline hydrochloride (described in Example 12) in 50 ml. of pyridine was treated with 4.8 g. (0.02 mole) of 3,4,5-trimethoxybenzoyl chloride, the solution heated on a steam bath for 6 and ½ hours and then allowed to stand over-night. The solid material which had separated was collected and recrystallized from ethanol/ether to give 7.1 g. of 1-methyl-3β-(3,4,5-trimethoxybenzoyloxymethyl)-5α-ethyl-1,2,3,4,4a,5,10,10a-octahydro-2,5-methanobenzo[g]quinoline hydrochloride, m.p. 247°–249°C.

B. Following a procedure similar to that described in Example 14A, using 7.9 g. (0.029 mole) of the 1-methyl-3β-hydroxymethyl-5α-ethyl-1,2,3,4,4a,5,10,10a-octahydro-2,5-methanobenzo[g]quinoline described in Example 12 and 80 ml. of propionic anhydride, and isolation of the product in the form of the hydrochloride salt, there was obtained 3.9 g. of 1-methyl-3β-propionyloxymethyl-5α-ethyl-1,2,3,4,4a,5,10,10a-octahydro-2,5-methanobenzo[g]quinoline hydrochloride, m.p. 264°–266°C. (from ethanol/ether).

Following a procedure similar to that described in Example 14A using the 1-methyl-3β-hydroxymethyl-5α-ethyl-1,2,3,4,4a,5,10,10a-octahydro-2,5-methanobenzo[g]quinoline described in Example 12 and an appropriate acid chloride in the presence of pyridine, the following compounds of formula II described in Table 14 are prepared where, in each instance, $R_1$ is $CH_3$; $R_2$, $R'_2$ and $R_3$ are hydrogen; $R_4$ is $C_2H_5$; and Y is $CH_2OR_7$.

Table 14

| Example | $R_7$ |
|---|---|
| 14C | 4-$CH_3C_6H_4CO$ |
| 14D | 4-$HOC_6H_4CO$ |
| 14E | 3-$ClC_6H_4CO$ |
| 14F | 3-$BrC_6H_4CO$ |
| 14G | 3-$FC_6H_4CO$ |
| 14H | 3-$CF_3C_6H_4CO$ |

EXAMPLE 15

A. A solution of 427 g. (0.97 mole) of ethyl 2-benzyl-3-(4-methoxybenzyl)-5-methyl-2-azabicyclo[2.2.2]oct-5-ene-7-carboxylate hydrochloride (described in Example 1H) was dissolved in 1,800 ml. of ethanol and reduced in two portions with hydrogen over 10 g. of palladium-on-charcoal. The product was worked up in the manner described above in Example 1AA to give 273 g. of ethyl 3-(4-methoxybenzyl)-5-methyl-2-azabicyclo-[2.2.2]oct-5-ene-7-carboxylate.

The latter was dissolved in 700 ml. of dry ethanol, and the solution added to a solution of 11 g. (0.48 mole) of sodium dissolved in 2 liters of dry ethanol. The resulting solution was stirred and refluxed for 72 hours, treated with 39 ml. of glacial acetic acid, cooled to room temperature and filtered through filter aid. The solution was evaporated to dryness, the solid residue was refluxed with ethyl acetate, the mixture was filtered, and the filtrate diluted with hexane to give one crop of 75 g. of product, m.p. 130°C. The filtrate, on extraction with dilute mineral acid, evaporation to dryness and recrystallization of the residue from ethyl acetate/hexane gave an additional 23 g. of product (total yield 98 g.), 2-(4-methoxybenzyl)-8-methylene-3-azabicyclo[3.3.1]-non-6-en-4-one. A small sample, recrystallized twice from ethyl acetate/hexane, gave material having m.p. 132°–133°C.

B. Following a procedure similar to that described in Example 15A, catalytic debenzylation of the ethyl 2,3-dibenzyl-5-methyl-2-azabicyclo[2.2.2]oct-5-ene-7-carboxylate hydrochloride described in Example 1F and base catalyzed rearrangement of the resulting ethyl 3-benzyl-5-methyl-2-azabicyclo[2.2.2]-oct-5-ene7-carboxylate affords 2-benzyl-8-methylene-3-azabicyclo[3.3.1]-non-6-en-4-one.

PREPARATION OF FINAL PRODUCTS

EXAMPLE

A. A solution of 11 g. (0.039 mole) of 1-methyl-3β-acetyl-5α-ethyl-1,2,3,4,4a,5,10,10a-octahydro-2,5-methanobenzo-[g]quinoline hydrochloride (described in Example 10A) in 20 ml. of a solution prepared by adding 89 ml. of trimethylamine to 94 ml. of formic acid was stirred and heated under reflux for about 15 minutes. The mixture was allowed to cool, diluted with 100 ml. of water and washed with 50 ml. of concentrated ammonium hydroxide and extracted twice with diethyl ether. The combined organic extracts, on washing once with water, drying and concentration to dryness, afforded 10 g. of a solid residue which was dissolved in about 30 ml. of absolute ethanol, the solution acidified with 13 ml. of ethereal hydrogen chloride, and diluted to 250 ml. with additional ether. The solid which separated was collected, washed, and set aside. (See Example 28A). The filtrate was washed with dilute ammonium hydroxide, dried, filtered and taken to dryness to give 3.1 g. of residue which was dissolved in diethyl ether and acidified with ethereal hydrogen chloride. The gummy, semi-crystalline material which separated was recrystallized from ethanol/ether to give 0.8 g. of 6(eq)-ethyl-1,2,3,4,5,6-hexahydro-3-methyl-11(eq)-(3-oxobutyl)-2,6-methano-3-benzazocine hydrochloride, m.p. 192°–196°C.

B. An alternative method for the preparation of the compounds of formula I from the compounds of formula II is illustrated by the following procedure:

A mixture of 10.0 g. (0.03 mole) of 1-methyl-3β-acetyl-5α-ethyl-7-hydroxy-1,2,3,4,4a,5,10,10a-octahydro-2,5-methanobenzo[g]quinoline described in Example 10C in 675 ml. of mesitylene and 25 ml. of formic acid was stirred and refluxed for about 8 hours while adding additional formic acid from time to time in order to maintain the pot temperature at 117°–119°C. The mixture was then cooled, extracted with dilute hydrochloric acid and the acid extracts washed first with diethyl ether, then basified with ammonium hydroxide and extracted once again with ethyl acetate. The organic extracts, on washing with brine, drying and evaporation to dryness, afforded 8.4 g. of solid which was recrystallized from ethyl acetate to give 3.7 g. of 6(eq)-ethyl-1,2,3,4,5,6-hexahydro-3-methyl-8-hydroxy-11(eq)-(3-oxobutyl)-2,6-methano-3-benzazocine, m.p. 190°–192°C.

Following a procedure similar to that described in Example 16A or B above, using an appropriate 7-$R_2$-8-$R'_2$-1-$R_1$-3-$COR_5$-4aα-$R_3$-5α-$R_4$-1,2,3,4,4a,5,10,10a-octahydro-2,5-methanobenzo[g]quinoline of formula II, the following 8-$R_2$-9-$R'_2$-6(eq)-$R_4$-1,2,3,4,5,6-hexahydro-3-$R_1$-11(az)-$R_3$-11(eq)-(oxo-lower-alkyl)-2,6-methano-3-benzazocines of formula I in Table 16a are prepared. The particular procedure used, that of Example 16A or 16B, is indicated by the letter designation (A) or (B), respectively, below the Example number. Unless noted otherwise, products were isolated as, and melting points recorded for, the free base form.

Table 16a

| Example | $R_1$/$CH_2Z$ | $R_2$/$R'_2$ | $R_3$/$R_4$ | Wt.II/Wt.I | m.p. (°C.)/Solv. |
|---|---|---|---|---|---|
| 16C | $CH_3$ | H | $CH_3$ | 10 (base) | 207–208 (a) |
| (A) | $CH_2CH_2COCH_3$ | H | $C_2H_5$ | 2.1 (salt) | ethanol/ether |
|  |  |  |  | (a) |  |
| 16D | $C_3H_5$—$CH_2$ (c) | H | H | 16 (base) | 206–208 (b) |
| (B) | $CH_2CH_2COCH_3$ | H | $C_2H_5$ | 7.8 (base) | ethanol/ether |
| 16E | $C_6H_5CH_2$ | $CH_3O$ | H | 18.8 (base) | 104–106 |
| (B) | $CH_2CH_2COCH_3$ | H | $CH_3$ | 7.2 (base) | ethanol |
| 16F | $C_6H_5CH_2$ | $CH_3O$ | H | 39 (base) | 122–125 |
| (B) | $CH_2CH_2COCH_3$ | H | $C_2H_5$ | 10.6 (base) | ethanol |
| 16G | $C_6H_5CH_2$ | $CH_3O$ | $CH_3$ | 19.5 (base) | 132–135 |
| (B) | $CH_2CH_2COCH_3$ | H | $CH_3$ | 11.5 (base) | ethanol |

(a) p-Toluenesulfonate hemihydrate
(b) Hydrochloride
(c) Cyclopropylmethyl

Following a procedure similar to that described in Example 16A or 16B above, using an appropriate 7-$R_2$-8-$R'_2$-1-$R_1$-3β-lower-alkanoyl-4aα-$R_3$-5α-$R_4$-1,2,3,4,4a,5,10,10a-octahydro-2,5-methanobenzo[g]quinoline of formula II, there are obtained the following 8-$R_2$-9-$R'_2$-6(eq)-$R_4$-1,2,3,4,5,6-hexahydro-3-$R_1$-11(ax)-$R_3$-11(eq)-(3-oxobutyl)-2,6-methano-3-benzazocines of formula I in Table 16b.

Table 16b

| Example | $R_1$/$CH_2Z$ | $R_2$/$R'_2$ | $R_3$/$R_4$ |
|---|---|---|---|
| 16H | $C_6H_5CH_2$ | H | H |
|  | $CH_2CH_2COCH_3$ | H | $C_2H_5$ |
| 16J | $CH_3$ | H | $CH_3$ |
|  | $CH_2CH_2COCH_3$ | H | $CH_3$ |
| 16K | $C_6H_5CH_2$ | H | H |
|  | $CH_2CH_2COOCH_3$ | H | $CH_3$ |
| 16L | $C_6H_5CH_2$ | HO | H |
|  | $CH_2CH_2COCH_3$ | H | $CH_3$ |
| 16M | $CH_3$ | H | H |
|  | $CH_2CH_2COC_3H_7$ | H | $C_2H_5$ |
| 16N | $C_6H_{11}$ | $CH_3S$ | H |
|  | $CH_2CH_2COCH_3$ | H | $CH_3$ |
| 16P | 4-$BrC_6H_4CH_2CH_2$ | $CH_3O$ | H |
|  | $CH_2CH_2COCH_3$ | H | $CH_3$ |
| 16Q | 4-$ClC_6H_4CH_2CH_2$ | $CH_3CONH$ | H |
|  | $CH_2CH_2COCH_3$ | H | $CH_3$ |
| 16R | 4-$FC_6H_4CH_2CH_2$ | $C_2H_5OCONH$ | H |
|  | $CH_2CH_2COCH_3$ | H | $CH_3$ |
| 16S | 4-Cl-3-$CH_3C_6H_3CH_2CH_2$ | H | H |
|  | $CH_2CH_2COCH_3$ | H | $CH_3$ |
| 16T | 3-$CH_3COOC_6H_4CH_2CH_2$ | H | H |
|  | $CH_2CH_2COCH_3$ | H | $CH_3$ |
| 16U | 3,4-$(CH_3O)_2C_6H_3CH_2CH_2$ | H | H |
|  | $CH_2CH_2COCH_3$ | H | $CH_3$ |
| 16V | 4-$CH_3SC_6H_4CH_2CH_2$ | H | H |
|  | $CH_2CH_2COCH_3$ | H | $CH_3$ |
| 16W | 3-$CF_3C_6H_4CH_2CH_2$ | H | H |
|  | $CH_2CH_2COCH_3$ | H | $CH_3$ |
| 16X | 3-$CH_3CONHC_6H_4CH_2CH_2$ | H | H |
|  | $CH_2CH_2COCH_3$ | H | $CH_3$ |
| 16Y | 3,4-$OCH_2OC_6H_3CH_2CH_2$ | H | H |
|  | $CH_2CH_2COCH_3$ | H | $CH_3$ |
| 16Z | $CH_3$ | H | H |
|  | $CH_2CH_2COCH_3$ | Cl | $CH_3$ |
| 16AA | $CH_3$ | H | H |
|  | $CH_2CH_2COCH_3$ | Br | $CH_3$ |
| 16BB | $CH_3$ | H | H |
|  | $CH_2CH_2COCH_3$ | F | $CH_3$ |
| 16CC | $CH_3$ | H | H |
|  | $CH_2CH_2COCH_3$ | $CF_3$ | $CH_3$ |
| 16DD | $CH_3$ | H | H |
|  | $CH_2CH_2COCH_3$ | $CH_3$ | $CH_3$ |
| 16EE | $CH_3$ | $C_6H_5$ | H |
|  | $CH_2CH_2COCH_3$ | H | $CH_3$ |
| 16FF | $CH_3$ | $CH_2{<}^O_O$ | H |
|  | $CH_2CH_2COCH_3$ |  | $CH_3$ |

Table 16b-continued

| Example | $R_1/CH_2Z$ | $R_2/R'_2$ | $R_3/R_4$ |
|---|---|---|---|
| 16GG | $CH_3$ | H | H |
|  | $CH_2CH_2COCH_3$ | H | H |
| 16HH | $CH_3$ | H | H |
|  | $CH_2CH_2COCH_3$ | H | $ClCH_2CH_2$ |
| 16JJ | $CH_3$ | H | $(CH_2)_3$ |
|  | $CH_2CH_2COCH_3$ | H |  |
| 16KK | $CH_3$ | H | $(CH_2)_4$ |
|  | $CH_2CH_2COCH_3$ | H |  |
| 16LL | $CH_3$ | H | H |
|  | $CH_2CH_2COCH_3$ | H | $CH_3OCH_2CH_2$ |
| 16MM | $CH_3$ | H | H |
|  | $CH_2CH_2COC_6H_5$ | H | $C_2H_5$ |
| 16NN | $CH_3$ | H | H |
|  | $CH_2CH_2COCH_3$ | H | $CH_2CH_2SC_6H_5$ |
| 16PP | $CH_3$ | H | H |
|  | $CH_2CH_2COCH_3$ | H | $CH_2CH_2SOC_6H_5$ |
| 16QQ | $CH_3$ | H | H |
|  | $CH_2CH_2COCH_3$ | H | $CH=CH_2$ |
| 16RR | $CH_3$ | H | H |
|  | $CH_2CH_2COCH_3$ | H | $CH_2CH_2SCH_3$ |
| 16SS | $CH_3$ | H | H |
|  | $CH_2CH_2COCH_3$ | H | $CH_2CH_2OH$ |

EXAMPLE 17

A solution of 27.0 g. (0.072 mole) of 3-benzyl-8-methoxy-6(eq)-methyl-1,2,3,4,5,6-hexahydro-11(eq)-(3-oxobutyl)-2,6-methano-3-benzazocine (described in Example 16E) was dissolved in 250 ml. of 48% hydrobromic acid and the mixture heated under reflux for about 11 hours. The mixture was concentrated to a small volume in vacuo, diluted with 100 ml. of water, concentrated again, and finally boiled with about 50 ml. of isopropanol. The solid which separated was collected and dried to give 23 g. of 3-benzyl-8-hydroxy-6(eq)-methyl-1,2,3,4,5,6-hexahydro-11(eq)-(3-oxobutyl)-2,6-methano-3-benzazocine hydrobromide, m.p. 156°–165°C.

EXAMPLE 18

A. A solution of 23.1 g. (0.05 mole) of 3-benzyl-8-hydroxy-6(eq)-methyl-1,2,3,4,5,6-hexahydro-11(eq)-(3-oxobutyl)-2,6-methano-3-benzazocine hydrobromide (described in Example 17) in 150 ml. of DMF was reduced with hydrogen over 1.0 g. of 10% palladium-on-charcoal using the procedure described above in Example 3. The product obtained was recrystallized from ethanol to give 16.1 g. of 8-hydroxy-6(eq)-methyl-1,2,3,4,5,6-hexahydro-11(eq)-(3-oxobutyl)-2,6-methano-3-benzazocine hydrobromide, m.p. 235°–237°C. (from ethanol).

B. In a similar fashion 21.2 g. of 3-benzyl-8-methoxy-6(eq)-methyl-1,2,3,4,5,6-hexahydro-11(eq)-(3-oxobutyl)-2,6-methano-3-benzazocine (described in Example 16e) was reduced with hydrogen over palladium-on-charcoal, and the product isolated in the form of the hydrochloride salt to give 11.4 g. of 8-methoxy-6(eq)-methyl-1,2,3,4,5,6-hexahydro-11(eq)-(3-oxobutyl)-2,6-methano-3-benzazocine hydrochloride, m.p. 189°–193°C. (from ethanol).

EXAMPLE 19

A. A mixture of 11.4 g. (0.03 mole) of 8-hydroxy-6(eq)-methyl-1,2,3,4,5,6-hexahydro-11(eq)-(3-oxobutyl)-2,6-methano-3-benzazocine hydrobromide (described in Example 18A), 5.4 g. of sodium bicarbonate and 5.2 g. (0.04 mole) of cyclopropylmethyl bromide in 150 ml. of DMF was heated under reflux for about nine hours and then concentrated to a small volume in vacuo. The residue was partitioned between ammonium hydroxide and ethyl acetate, the organic layer separated, and the aqueous layer extracted with additional portions of ethyl acetate. The combined extracts were washed once with water, then with brine, dried, filtered and taken to dryness to give 12.1 g. of crude product which was converted to the hydrochloride salt. The latter was recrystallized once from acetonitrile and once from ethanol/ether to give 5.2 g. of 3-cyclopropylmethyl-8-hydroxy-6(eq)-methyl-1,2,3,4,5,6-hexahydro-11(eq)-(3-oxobutyl)-2,6-methano-3-benzazocine hydrochloride, m.p. 147°–154°C.

B. Following a procedure similar to that described in Example 19A, 3-cyclopropylmethyl-8-methoxy-6(eq)-methyl-1,2,3,4,5,6-hexahydro-11(eq)-(3-oxobutyl)-2,6-methano-3-benzazocine (12.9 g.) was prepared by reaction of 15.0 g. (0.04 mole) of 8-methoxy-6(eq)-methyl-1,2,3,4,5,6-hexahydro-11(eq)-(3-oxobutyl)-2,6-methano-3-benzazocine (described in Example 18B) with cyclopropylmethyl bromide in the presence of sodium bicarbonate in DMF.

C. 3,6(eq)-Dimethyl-8-hydroxy-1,2,3,4,5,6-hexahydro-11(eq)-(3-oxobutyl)-2,6-methano-3-benzazocine p-toluenesulfonate (9.9 g.) m.p. 199°–201°C. (from ethanol), was prepared by reductive alkylation of 8-hydroxy-6(eq)-methyl-1,2,3,4,5,6-hexahydro-11(eq)-(3-oxobutyl)-2,6-methano-3-benzazocine (11.4 g.) hydrobromide (described in Example 18A) with formaldehyde and triethylamine over palladium-on-charcoal in ethanol under about 50 pounds p.s.i. of hydrogen using the procedure described in Example 35.

D. 3,6(eq)-Dimethyl-8-methoxy-1,2,3,4,5,6-hexahydro-11(eq)-(3-oxobutyl)-2,6-methano-3-benzazocine (7.5 g.) was prepared by reductive alkylation of 8.2 g. of 8-methoxy-6(eq)-methyl-1,2,3,4,5,6-hexahydro-11(eq)-(3-oxobutyl)-2,6-methano-3-benzazocine hydrochloride (described in Example 18B) with formaldehyde and triethylamine over palladium-on-charcoal in ethanol under about 50 pounds p.s.i. of hydrogen using the procedure described in Example 35.

Following a procedure similar to that described in Example 19A, using the 8-hydroxy-6(eq)-methyl-1,2,3,4,5,6-hexahydro-11(eq)-(3-oxobutyl)-2,6-methano-3-benzazocine described in Example 18A and an appropriate alkylating agent, $R_1Hal$, there are prepared the following compounds of formula I in Table 19, where in each instance $R_2$ is HO; $R'_2$ and $R_3$ are each hydrogen; $R_4$ is $CH_3$; and $CH_2Z$ is $CH_2CH_2COCH_3$.

Table 19

| Example | $R_1$ |
|---|---|
| 19E | $CH_2=CHCH_2$ |
| 19F | $(CH_3)_2C=CHCH_2$ |
| 19G | $CH\quad CCH_2$ |
| 19H | $CH_3C\quad CCH_2$ |
| 19J | $Cl_2C=CHCH_2$ |

EXAMPLE 20

A. A solution of 4.7 g. (0.16 mole) of 6(eq)-ethyl-1,2,3,4,5,6-hexahydro-3-methyl-11(eq)-(3-oxobutyl)-2,6-methano-3-benzazocine (from the hydrochloride described in Example 16A) in 28 ml. of diethyl ether was added dropwise with stirring to 28 ml. (0.05 mole) of a 1.8M solution of methyl lithium in diethyl ether. The mixture was stirred under nitrogen for about 1 hour, poured into an ice/aqueous ammonium chloride solution, and the ether layer separated and washed with water. The organic layer was dried, filtered, and taken to dryness to give 4.9 g. of residue which was converted to the methanesulfonate salt in methanol/diethyl ether. The latter was recrystallized from methanol/diethyl ether to give 2.5 g. of 3-methyl-6(eq)-ethyl-1,2,3,4,5,6-hexahydro-11(eq)-(3-methyl-3hydroxybutyl)-2,6-methano-3-benzazocine methanesulfonate, m.p. 173°–174°C.

Following a procedure similar to that described in Example 20A, using the 8-$R_2$-6(eq)-$R_4$-1,2,3,4,5,6-hexahydro-3-$R_1$-11(eq)-(3-oxobutyl)-2,6-methano-3-benzazocines described in Examples 16B, 16D, 19A, 16E, 19C, 19D, 16E, 19A, 16E and 16G, and an appropriate lower-alkyl lithium ($R_6Li$), there are prepared the respective 8-$R_2$-6(eq)-$R_4$-1,2,3,4,5,6-hexahydro-3-$R_1$-11(eq)-(3-methyl-3-hydroxy-lower-alkyl)-2,6-methano-3-benzazocines of formula I in Table 20a where, in each instance, $R'_2$, $R_3$ and $R_7$ are hydrogen and $R_5$ is $CH_3$. Unless noted otherwise, products were isolated as, and melting points recorded for, the free base form.

Table 20a

| Example | $R_1/R_2$ | $R_4/R_6$ | Wt.S.M./Wt.Prod. | m.p. (°C.)/Solv. |
|---|---|---|---|---|
| 20B | $CH_3$ | $C_2H_5$ | 3.6 (base) | 203–206 |
|  | HO | $CH_3$ | 1.2 (base) | ethyl acetate |
| 20C | $C_3H_5$—$CH_2$ (a) | $C_2H_5$ | 4.0 (base) | 184–186 (b) |
|  | H | $CH_3$ | 2.2 (b) | $CH_3CN$/ether |
| 20D | $C_3H_5$—$CH_2$ (a) | $CH_3$ | 11.4 (base) | 138–140 |
|  | HO | $CH_3$ | 3.3 (base) | ethyl acetate |
| 20E | $C_6H_5CH_2$ | $CH_3$ | 3.78 (base) | 252 (b) |
|  | $CH_3O$ | $t$-$C_4H_9$ | 1.25 (b) | ethanol |
| 20F | $CH_3$ | $CH_3$ | 4.2 (base) | 182–183 |
|  | HO | $CH_3$ | 2.6 (base) | ethyl acetate |
| 20G | $CH_3$ | $CH_3$ | 7.5 g. (base) | oil |
|  | $CH_3O$ | $C_4H_9$ | 11.3 g. (base) |  |
| 20H | $C_6H_5CH_2$ | $CH_3$ | 3.78 (base) | oil |
|  | $CH_3O$ | $C_2H_5$ | 4.5 (base) |  |
| 20J | $C_3H_5$—$CH_2$ (a) | $CH_3$ | 13.4 (base) | 184–185 (c) |
|  | HO (d) | $C_4H_9$ | 10.2 (c) | ethanol/ether |
| 20K | $C_6H_5CH_2$ | $CH_3$ | 20.0 (base) | oil |
|  | $CH_3O$ | $C_3H_7$ | 21.8 (base) |  |
| 20L | $C_6H_5CH_2$ | $CH_3$ (e) | 11.5 (base) | 223–227 (b) |
|  | $CH_3O$ | $t$-$C_4H_9$ | 2.4 (b) | ethanol/ether |

(a) Cyclopropylmethyl
(b) Hydrochloride
(c) Methanesulfonate
(d) Starting material was methyl ether described in Example 19B, and the product obtained from reaction with butyl lithium was cleaved, without characterization, to the 8-HO compound with sodium propanethiol using the procedure described in Example 24A.
(e) $R_3$ is $CH_3$ Following a procedure similar to that described in Example 20A, using the 8-$R_2$-6(eq)-$R_4$-1,2,3,4,5,6-hexahydro-3-$R_1$-11(ax)-$R_3$-11(eq)—$CH_2CH_2COR_5$-2,6-methano-3-benzazocines described in Examples 16N, 16P, 16Q, 16R, 16S, 16T, 16U, 16V, 16W, 16X, 16Y, 16MM, 16A and 16C, and an appropriate lower-alkyl, phenyl or phenyl-lower-alkyl lithium, $R_6Li$, there are obtained the respective 8-$R_2$-6(eq)-$R_4$-1,2,3,4,5,6-hexahydro-3-$R_1$-11(eq)—$CH_2CH_2C(R_5)$—($R_6$)OH-2,6-methano-3-benzazocines of formula I listed in Table 20b where, in each instance, $R'_2$ and $R_7$ are hydrogen.

Table 20b

| Example | $R_1$ | $R_2$ | $R_3$ | $R_4$ | $R_5$ | $R_6$ |
|---|---|---|---|---|---|---|
| 20M | $C_6H_{11}$ | $CH_3S$ | H | $CH_3$ | $CH_3$ | $CH_3$ |
| 20N | 4-$BrC_6H_4CH_2CH_2$ | $CH_3O$ | H | $CH_3$ | $CH_3$ | $CH_3$ |
| 20P | 4-$ClC_6H_4CH_2CH_2$ | $CH_3CONH$ | H | $CH_3$ | $CH_3$ | $CH_3$ |
| 20Q | 4-$FC_6H_4CH_2CH_2$ | $C_2H_5OCONH$ | H | $CH_3$ | $CH_3$ | $CH_3$ |
| 20R | 4-Cl-3-$CH_3C_6H_3CH_2CH_2$ | H | H | $CH_3$ | $CH_3$ | $CH_3$ |
| 20S | 3-$CH_3COOC_6H_4CH_2CH_2$ | H | H | $CH_3$ | $CH_3$ | $CH_3$ |
| 20T | 3,4-$(CH_3O)_2C_6H_3CH_2CH_2$ | H | H | $CH_3$ | $CH_3$ | $CH_3$ |
| 20U | 4-$CH_3SC_6H_4CH_2CH_2$ | H | H | $CH_3$ | $CH_3$ | $CH_3$ |
| 20V | 3-$CF_3C_6H_4CH_2CH_2$ | H | H | $CH_3$ | $CH_3$ | $CH_3$ |
| 20W | 3-$CH_3CONHC_6H_4CH_2CH_2$ | H | H | $CH_3C-H_3$ | $CH_3$ |  |
| 20X | 3,4-$OCH_2OC_6H_3CH_2CH_2$ | H | H | $CH_3$ | $CH_3$ | $CH_3$ |
| 20Y | $CH_3$ | H | H | $C_2H_5$ | $C_6H_5$ | $CH_3$ |
| 20Z | $CH_3$ | H | H | $C_2H_5$ | $CH_3$ | $C_6H_5$ |
| 20AA | $CH_3$ | H | $CH_3$ | $C_2H_5$ | $CH_3$ | $C_6H_5CH_2CH_2$ |

EXAMPLE 21

A. Reaction of the 3-[2-(4-fluorophenyl)ethyl]-8-ethoxy-carbonylamino-6(eq)-methyl-1,2,3,4,5,6-hexahydro-11(eq)-(3-methyl-3-hydroxybutyl)-2,6-methano-3-benzazocine (described in Example 20Q) with aqueous alkali in ethanol affords 3-[2-(4-fluorophenyl)ethyl]-8-amino-6(eq)-methyl-1,2,3,4,5,6-hexahydro-11(eq)-(3-methyl-3-hydroxybutyl)-2,6-methano-3-benzazocine.

Following a procedure similar to that described in Example 21A, the following 8-$R_2$-6(eq)-$R_4$-1,2,3,4,5,6-hexahydro-3-$R_1$-11(eq)-(3-methyl-3-hydroxy-loweralkyl)-2,6-methano-3-benzazocines of formula I are also prepared:

B. 3-[2-(3-Hydroxyphenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetoxyphenyl)ethyl]-6-(eq)-methyl-1,2,3,4,5,6-hexahydro-11(eq)-(3-methyl-3-hydroxybutyl)-2,6-methano-3-benzazocine (described in Example 20S); and C. 3-[2-(3-Aminophenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetylaminophenyl)ethyl]-6(eq)-methyl-1,2,3,4,5,6-hexahydro-11(eq)-(3-methyl-3-hydroxybutyl)-2,6-methano-3-benzazocine (described in Example 20W).

EXAMPLE 22

A. Reaction of 8-hydroxy-3,6(eq)-dimethyl-1,2,3,4,5,6-hexahydro-11(eq)-(3-methyl-3-hydroxybutyl)-2,6-methano-3-benzazocine (described in Example 20F) with acetic anhydride affords 8-acetoxy-3,6(eq)-dimethyl-1,2,3,4,5,6-hexahydro-11(eq)-(3-methyl-3-acetoxybutyl)-2,6-methano-3-benzazocine.

Following a procedure similar to that described in Example 22A, using the 3-methyl-6(eq)-ethyl-1,2,3,4,5,6-hexahydro-11(eq)-(3-methyl-3-hydroxybutyl)-2,6-methano-3-benzazocine described in Example 20A and an appropriate acid chloride in the presence of pyridine, there are obtained the following 3-methyl-6(eq)-ethyl-1,2,3,4,5,6-hexahydro-11(eq)-(3-methyl-3-$R_7$O-butyl)-2,6-methano-3-benzazocines of formula I in Table 22 where, in each instance, $R_1$, $R_5$ and $R_6$ are $CH_3$; $R_2$, $R'_2$ and $R_3$ are each hydrogen; and $R_4$ is $C_2H_5$.

Table 22

| Example | $R_7$ |
|---|---|
| 22B | $C_6H_5CO$ |
| 22C | $4\text{-}CH_3C_6H_4CO$ |
| 22D | $3\text{-}CH_3OC_6H_4CO$ |
| 22E | $4\text{-}ClC_6H_4CO$ |
| 22F | $4\text{-}BrC_6H_4CO$ |
| 22G | $4\text{-}FC_6H_4CO$ |
| 22H | $3\text{-}CF_3C_6H_4CO$ |

EXAMPLE 23

Reaction of 3-cyclopropylmethyl-6(eq)-ethyl-1,2,3,4,5,6-hexahydro-11(eq)-(3-oxobutyl)-2,6-methano-3-benzazocine (described in Example 16D) with sodium borohydride in methanol affords 3-cyclopropylmethyl-6(eq)-ethyl-1,2,3,4,5,6-hexahydro-11(eq)-(3-hydroxybutyl)-2,6-methano-3-benzazocine.

EXAMPLE 24

A. A solution of 4.72 g. (0.01 mole) of 3-benzyl-6(eq)-methyl-8-methoxy-1,2,3,4,5,6-hexahydro-11(eq)-(3-hydroxy-3,4,4-trimethylpentyl)-2,6-methano-3-benzazocine (described in Example 20E) in 50 ml. of DMF was reduced with hydrogen over 0.5 g. of palladium-on-charcoal under a hydrogen pressure of about 50 pounds p.s.i. using the procedure described in Example 3. When reduction was complete, the catalyst was removed by filtration, and the solution, containing 6(eq)-methyl-8-methoxy-1,2,3,4,5,6-hexahydro-11(eq)-(3-hydroxy-3,4,4-trimethylpentyl)-2,6-methano-3-benzazocine was treated with 1.68 g. (0.02 mole) of sodium bicarbonate and 2.0 g. (0.015 mole) of cyclopropylmethyl bromide, and the mixture was warmed with stirring on a steam bath for 1 hour.

The reaction mixture containing crude 3-cyclopropylmethyl-6(eq)-methyl-8-methoxy-1,2,3,4,5,6-hexahydro-11(eq)-(3-hydroxy-3,4,4-trimethylpentyl)-2,6-methano-3-benzazocine, was distilled at atmospheric pressure, collecting 25 ml. of distillate, and then treated with 2.1 g. (0.05 mole) of a 57% dispersion of sodium hydride in mineral oil and 5 ml. of DMF. The mixture was cooled in an ice bath and treated dropwise with stirring under nitrogen with 4.6 ml. of propanethiol. After refluxing and stirring for about four hours, the reaction mixture was poured into a solution of aqueous ammonium chloride and extracted with 50 ml. of diethyl ether. The product was isolated in the usual manner in the form of the free base which was recrystallized from ethanol to give 2.4 g. of 3-cyclopropylmethyl-6(eq)-methyl-8-hydroxy-1,2,3,4,5,6-hexahydro-11(eq)-(3-hydroxy-3,4,4-trimethylpentyl)-2,6-methano-3-benzazocine, m.p. 195°–198°C. The methanesulfonate gave m.p. 232°C.

Following a procedure similar to that described in Example 24A, using the 8-methoxy-6(eq)-methyl-1,2,3,4,5,6-hexahydro-3-benzyl-11(ax)-$R_3$-11(eq)-(3-hydroxy-3-methyl-lower-alkyl)-2,6-methano-3-benzazocines described in Examples 20E, 20K, 20L and 20K, and an appropriate alkylating agent, $R_1$-Hal, (or reductive alkylation with formaldehyde and formic acid using the procedure described in Example 35), there are obtained the respective 8-hydroxy-6(eq)-methyl-1,2,3,4,5,6-hexahydro-3-$R_1$-11(ax)-$R_3$-11(eq)-(3-hydroxy-3-methyl-lower-alkyl)-2,6-methano-3-benzazocines of formula I in Table 24 where, in each instance, $R_2$ is hydroxy; $R'_2$ and $R_7$ are each hydrogen; and $R_4$ and $R_5$ are each $CH_3$. Melting points are given in each case for the methanesulfonate salt, and yields are also given for the methanesulfonate unless noted otherwise.

Table 24

| Example | $R_1$ | $R_3/R_6$ | Wt.S.M./Wt.Prod. | m.p. (°C.)/Solv. |
|---|---|---|---|---|
| 24B | $CH_3$ | H | 4.72 (HCl) | 206–208 |
|  |  | $t\text{-}C_4H_9$ | 2.7 | methanol/ether |
| 24C | $CH_3$ | H | 10.9 (base) | 144–146 |
|  |  | $C_3H_7$ | 7.4 (base) | acetone |
| 24D | $C_3H_5\text{—}CH_2$ (a) | $CH_3$ | 2.5 (HCl) | 249–252 |

Table 24-continued

| Example | R₁ | R₃/R₆ | Wt.S.M./Wt.Prod. | m.p. (°C.)/Solv. |
|---|---|---|---|---|
| 24E | C₃H₅—CH₂ (a) | t-C₄H₉ | 1.4 | methanol/ether |
|  |  | H | 9.2 (base) | 182–183 |
|  |  | C₃H₇ | 1.8 | ethanol/ether |

(a) Cyclopropylmethyl

EXAMPLE 25

A. A solution of 15 g. (0.04 mole) of 3-benzyl-8-methoxy-6(eq)-methyl-1,2,3,4,5,6-hexahydro-11(eq)-(3-oxobutyl)-2,6-methano-3-benzazocine (described in Example 16E) was catalytically debenzylated and the resulting nor-base alkylated with cyclopropylmethyl bromide in the presence of sodium bicarbonate using the procedure described in Example 24A. The resulting 3-cyclopropylmethyl-8-methoxy-6(eq)-methyl-1,2,3,4,5,6-hexahydro-11(eq)-(3-oxobutyl)-2,6-methano-3-benzazocine (12.9 g.) was dissolved in 125 ml. of toluene and added to 45 ml. of a 2.1M solution of n-butyl lithium in hexane at −65°C. using the procedure described in Example 20A. The resulting 3-cyclopropylmethyl-8-methoxy-6(eq)-methyl-1,2,3,4,5,6-hexahydro-11(eq)-(3-hydroxy-3-methylheptyl)-2,6-methano-3-benzazocine (13.4 g.) was dissolved in 130 ml. of DMF and the ether group cleaved by treatment with 7.1 g. (0.168 mole) of a 57% mineral oil dispersion of sodium hydride and 12.8 g. (0.168 mole) of propanethiol in the manner described above in Example 24A. The product was converted to the methanesulfonate salt which was recrystallized from ethanol/ether to give 10.2 g. of 3-cyclopropylmethyl-8-hydroxy-6(eq)-methyl-1,2,3,4,5,6-hexahydro-11(eq)-(3-hydroxy-3-methylheptyl)-2,6-methano-3-benzazocine methanesulfonate, m.p. 184°–185°C.

Following a procedure similar to that described in Example 25A, using the 3-benzyl-8-methoxy-6(eq)-methyl-1,2,3,4,5,6-hexahydro-11(eq)-(3-oxobutyl)-2,6-methano-3-benzazocine described in Example 16E, ethyl lithium and an appropriate alkylating agent, R-Hal, (or reductive alkylation with formaldehyde and formic acid using the procedure described in Example 35), there are obtained the 8-hydroxy-3-R₁-6(eq)-methyl-1,2,3,4,5,6-hexahydro-11(eq)-(3-hydroxy-3-methylpentyl)-2,6-methano-3-benzazocines of formula I in Table 25 where, in each instance, R₂ is hydroxy; R′₂, R₃ and R₇ are hydrogen; R₄ and R₅ are CH₃; and R₆ is C₂H₅. In each instance, the melting points are given for the methanesulfonate salt, and the yield of product is given for a free base.

crystallized from ethanol/ether to give 2.6 g. of 3-methyl-8-hydroxy-6(eq)-methyl-1,2,3,4,5,6-hexahydro11-(eq)-(3-hydroxy13-methylheptyl)-2,6-methano-3-benzazocine methanesulfonate, m.p. 184°–186°C.

EXAMPLE 27

A. A solution of 1.8 g. (0.0046 mole) of 1-benzyl-3β-(2-hydroxy-2-propyl)-5α-methyl-7-methoxy-1,2,3,4,4a,5,10,10a-octahydro-2,5-methanobenzo[g]quinoline hydrochloride (described in Example 11D) was dissolved in 100 ml. of mesitylene and the solution treated with 3.8 ml. (0.1 mole) of formic acid and refluxed and stirred for about twenty-four hours. On cooling, the mixture was extracted with 3 ml. portions of 1M phosphoric acid, and the combined aqueous extracts washed twice with diethyl ether and then basified by the cautious addition of 6.6 g. of potassium hydroxide pellets. The oil which separated was extracted with diethyl ether, and the ether extracts worked up in the usual manner to give an oil which was converted to the hydrochloride salt. The latter was recrystallized from ethanol/ether to give 0.3 g. of 3-benzyl-6(eq)-methyl-8-methoxy-1,2,3,4,5,6-hexahydro-11(eq)-(3-methyl-2-butenyl)-2,6-methano-3-benzazocine hydrochloride, m.p. 232°14 235°C.

B. Following a procedure similar to that described in Example 27A, 19.6 g. (0.062 mole) of 1-methyl-3β-(2-hydroxy-2-propyl)-5α-methyl-7-methoxy-1,2,3,4,4a5,10,10a-octahydro-2,5-methanobenzo[g]quinoline described in Example 9F in 1 liter of mesitylene and 38 ml. of formic acid was heated and stirred under reflux for 24 hours and worked up in the manner described in Example 27A to give 8.5 g. (0.028 mole) of 3,6(eq)-dimethyl-8-methoxy-1,2,3,4,5,6-hexahydro-11(eq)-(3-methyl-2-butenyl)-2,6-methano-3-benzazocine as an oil which, without further characterization, was cleaved with 0.15 mole of sodium propylsulfide in 75 ml. of DMF using the procedure described in Example 24A. The product was converted to the methanesulfonate salt which was recrystallized from ethanol to give 1.6 g. of 3,6(eq)-dimethyl-8-hydroxy-1,2,3,4,5,6-hexahydro-11(eq)-(3-methyl-2-butenyl)-2,6-methano-3-benzazocine methanesulfonate, m.p. 226°–229°C.

Following a procedure similar to that described in

Table 25

| Example | R₁ | Wt.S.M./Wt.Prod. | m.p. (°C.)/Solv. |
|---|---|---|---|
| 25B | cyclopropyl-CH₂ | 15.0 (base) | 195–196 |
|  |  | 8.3 (base) | acetone |
| 25C | CH₃ | 15.0 (base) | 155–157 |
|  |  | 11.0 (base) | ethanol |

EXAMPLE 26

A 5.7 g. sample of 3-methyl-8-methoxy-6(eq)-methyl-1,2,3,4,5,6-hexahydro-11(eq)-(3-hydroxy-3-methylheptyl)-2,6-methano-3-benzazocine described in Example 20G in DMF was cleaved with sodium propylsulfide (0.063 mole) using the procedure described in Example 24A and the product (3.4 g. of crude base) converted to the methanesulfonate salt which was re- Example 27A, using the 7-R₂-1-R₁-3-C(R₅)(R₆)OR₇-4aα-R₃-5α-R₄-1,2,3,4,4a,5,10,10a-octahydro-2,5-methanobenzo[g]quinolines described in Examples 9A, 9B, 9C, 9D, 9G, 9E, 11A, 11C and 13A in refluxing mesitylene/formic acid, there are obtained the respective 8-R₂-6(eq)-R₄-1,2,3,4,5,6-hexahydro-3-R₁-11(ax)-R₃-11(eq)-(2-lower-alkenyl)-2,6-methano-3-benzazocines of formula I in Table 27 where, in each instance, R′₂ is hydrogen.

Table 27

| Example | $R_1$ | $R_2$ | $R_3$ | $R_4$ | $R_5$ | $R_6$ |
|---|---|---|---|---|---|---|
| 27C | $CH_3$ | H | H | $C_3H_7$ | $CH_3$ | $CH_3$ |
| 27D | $CH_3$ | H | H | $C_2H_5$ | $CH_3$ | $CH_3$ |
| 27E | $CH_3$ | H | H | $CH_3$ | $CH_3$ | $CH_3$ |
| 27F | $CH_3$ | HO | H | $C_2H_5$ | $CH_3$ | $CH_3$ |
| 27G | cyclopropyl-$CH_2$ | H | H | $C_2H_5$ | $CH_3$ | $CH_3$ |
| 27H | $C_6H_5CH_2CH_2$ | H | H | $C_2H_5$ | $CH_3$ | $CH_3$ |
| 27J | $CH_3$ | H | H | $C_2H_5$ | $CH_3$ | $C_3H_7$ |
| 27K | $CH_3$ | H | $CH_3$ | $C_2H_5$ | $CH_3$ | $CH_3$ |
| 27L | $CH_3$ | H | H | $C_2H_5$ | $CH_3$ | H |

EXAMPLE 28

A. Two grams of the solid hydrochloride salt obtained as an initial precipitate from the ethanol/ether crystallization in Example 16A was recrystallized once again from ethanol/ether to give 1.3 g. of 1,2-dimethyl-5α-ethyl-1,2,3,4,4a,5,10,10a-octahydro-3,5-ethenobenzo[g]quinoline hydrochloride, m.p. 262°–264°C.

A solution of 5.3 g. (0.017 mole) of the latter in 50 ml. of ethanol was reduced with 0.1 g. of platinum oxide. When reaction was complete, the catalyst was removed by filtration, and the product isolated in the form of the hydrochloride salt in the usual manner to give 2.4 g. of 1,2-dimethyl-5α-ethyl-1,2,3,4,4a,5,10,-10a-octahydro-3,5-ethanobenzo[g]quinoline hydrochloride, m.p. 319°–329°C.

The following 1-$R_1$-2-methyl-4aα-$R_3$-5α-ethyl-1,2,3,4,4a,5,10,10a-octahydro-3,5-ethenobenzo[g]quinolines of formula IIIa in Table 28a where, in each instance, $R_2$ and $R'_2$ are hydrogen; $R_4$ is $C_2H_5$ and

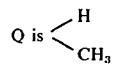

were obtained as by-products with the main products of Examples 16C and 16D, respectively. The yields and melting points for the compounds of Examples 28B and 28C are given for the hydrochloride and p-toluenesulfonate salts, respectively.

Table 28a

| Example | $R_1$ | $R_3$ | Wt.II/Wt.IIIa | m.p. (°C.)/Solv. |
|---|---|---|---|---|
| 28B | $CH_3$ | $CH_3$ | 10 (base) 1.2 | 234–235 acetone |
| 28C | cyclopropyl-$CH_2$ | H | 16 (base) 2.5 | 187–189 ethyl acetate |

The following 1-$R_1$-2-Q-4aα-$R_3$-5α-$R_4$-7-$R_2$-8-$R'_2$-1,2,3,4,4a,5,10,10a-octahydro-3,5-ethenobenzo[g]quinolines of formula IIIa are obtained as by-products from the preparations described, respectively, in Examples 16E, 16H, 16M, 16N, 16P, 16Q, 16R, 16S, 16T, 16U, 16V, 16W, 16X, 16Y, 16Z, 16AA, 16BB, 16CC, 16DD, 16EE, 16FF, 16GG, 16HH, 16JJ, 16KK, 16LL, 16NN, 16PP, 16QQ, 16RR, 16SS and 10D.

Table 28b

| Example | $R_1$/Q | $R_2$/$R'_2$ | $R_3$/$R_4$ |
|---|---|---|---|
| 28D | $C_6H_5CH_2$ | $CH_3O$ | H |
|  | $CH_3$ | H | $CH_3$ |
| 28E | $C_6H_5CH_2$ | H | H |
|  | $CH_3$ | H | $C_2H_5$ |
| 28F | $CH_3$ | H | H |
|  | $C_3H_7$ | H | $C_2H_5$ |
| 28G | $C_6H_{11}$ | $CH_3S$ | H |
|  | $CH_3$ | H | $CH_3$ |
| 28H | 4-$BrC_6H_4CH_2CH_2$ | $CH_3O$ | H |
|  | $CH_3$ | H | $CH_3$ |
| 28J | 4-$ClC_6H_4CH_2CH_2$ | $CH_3CONH$ | H |
|  | $CH_3$ | H | $CH_3$ |
| 28K | 4-$FC_6H_4CH_2CH_2$ | $C_2H_5OCONH$ | H |
|  | $CH_3$ | H | $CH_3$ |
| 28L | 4-Cl-3-$CH_3C_6H_3CH_2CH_2$ | H | H |
|  | $CH_3$ | H | $CH_3$ |
| 28M | 3-$CH_3COOC_6H_4CH_2CH_2$ | H | H |
|  | $CH_3$ | H | $CH_3$ |
| 28N | 3,4-$(CH_3O)_2C_6H_3CH_2CH_2$ | H | H |
|  | $CH_3$ | H | $CH_3$ |
| 28P | 4-$CH_3SC_6H_4CH_2CH_2$ | H | H |
|  | $CH_3$ | H | $CH_3$ |
| 28Q | 3-$CF_3C_6H_4CH_2CH_2$ | H | H |
|  | $CH_3$ | H | $CH_3$ |
| 28R | 3-$CH_3CONHC_6H_4CH_2CH_2$ | H | H |
|  | $CH_3$ | H | $CH_3$ |
| 28S | 3,4-$OCH_2OC_6H_3CH_2CH_2$ | H | H |
|  | $CH_3$ | H | $CH_3$ |
| 28T | $CH_3$ | H | H |
|  | $CH_3$ | Cl | $CH_3$ |
| 28U | $CH_3$ | H | H |
|  | $CH_3$ | Br | $CH_3$ |
| 28V | $CH_3$ | H | H |
|  | $CH_3$ | F | $CH_3$ |
| 28W | $CH_3$ | H | H |
|  | $CH_3$ | $CF_3$ | $CH_3$ |
| 28X | $CH_3$ | H | H |

Table 28b-continued

| Example | $R_1/Q$ | $R_2/R'_2$ | $R_3/R_4$ |
|---|---|---|---|
|  | $CH_3$ | $CH_3$ | $CH_3$ |
| 28Y | $CH_3$ | $C_6H_5$ | H |
|  | $CH_3$ | H | $CH_3$ |
| 28Z | $CH_3$ | $CH_2{<}^O_O$ | H |
|  | $CH_3$ |  | $CH_3$ |
| 28AA | $CH_3$ | H | H |
|  | $CH_3$ | H | H |
| 28BB | $CH_3$ | H | H |
|  | $CH_3$ | H | $ClCH_2CH_2$ |
| 28CC | $CH_3$ | H | $(CH_2)_3{<}$ |
|  | $CH_3$ | H |  |
| 28DD | $CH_3$ | H | $(CH_2)_4{<}$ |
|  | $CH_3$ | H |  |
| 28EE | $CH_3$ | H | H |
|  | $CH_3$ | H | $CH_3OCH_2CH_2$ |
| 28FF | $CH_3$ | H | H |
|  | $CH_3$ | H | $CH_2CH_2SC_6H_5$ |
| 28GG | $CH_3$ | H | H |
|  | $CH_3$ | H | $CH_2CH_2SOC_6H_5$ |
| 28HH | $CH_3$ | H | H |
|  | $CH_3$ | H | $CH=CH_2$ |
| 28JJ | $CH_3$ | H | H |
|  | $CH_3$ | H | $CH_2CH_2SCH_3$ |
| 28KK | $CH_3$ | H | H |
|  | $CH_3$ | H | $CH_2CH_2OH$ |
| 28LL | $CH_3$ | H | H |
|  | $C_6H_5$ | H | $C_2H_5$ |

Reduction of the compounds in Table 28b with hydrogen over platinum oxide using the procedure described in Example 28A affords the corresponding 1-$R_1$-2-Q-4a$\alpha$-$R_3$-5$\alpha$-$R_4$-7-$R_2$-8-$R'_2$-1,2,3,4,4a,5,10,10a-octahydro-3,5-ethanobenzo[g]quinolines of formula IIIb.

EXAMPLE 29

A. Hydrolysis with aqueous alkali in an ethanol solvent of 1-[2-(4-chlorophenyl)ethyl]-7-acetylamino-2,5$\alpha$-dimethyl-1,2,3,4,4a,5,10,10a-octahydro-3,5-ethenobenzo[g]quinoline and 1-[2-(4-chlorophenyl)ethyl]-7-acetylamino-2,5$\alpha$-dimethyl-1,2,3,4,4a,5,10,-10a-octahydro-3,5-ethanobenzo[g]quinoline (described in Example 28J) affords, respectively, 7-amino-1-[2-(4-chlorophenyl)ethyl]-2,5$\alpha$-dimethyl-1,2,3,4,4a,5,10,10a-octahydro-3,5-ethenobenzo[g]-quinoline and 7-amino-1-[2-(4-chlorophenyl)ethyl]-2,5$\alpha$-dimethyl-1,2,3,4,4a,5,10,10a-octahydro-3,5-ethanobenzo[g]quinoline.

Following a procedure similar to that described in Example 29A, the following compounds of formulas IIIa and IIIb are similarly prepared:

B. 7-Amino-1-[2-(4-fluorophenyl)ethyl]-2,5$\alpha$-dimethyl-1,2,3,4,4a,5,10,10-octahydro-3,5-ethenobenzo[g]quinoline and 7-amino-1-[2-(4-fluorophenyl)ethyl]-2,5$\alpha$-dimethyl-1,2,3,4,4a,5,10,10a-octahydro-3,5-ethanobenzo[g]quinoline, by alkaline saponification, respectively, of 1-[2-(4-fluorophenyl)ethyl]-2,5$\alpha$-dimethyl-7-ethoxycarbonylamino-1,2,3,4,4a,5,10,10a-octahydro-3,5-ethenobenzo[g]quinoline and 1-[2-(4-fluorophenyl)ethyl]-2,5$\alpha$-dimethyl-7-ethoxycarbonylamino-1,2,3,4,4a,5,10,10a-octahydro-3,5-ethanobenzo-[g]quinoline (described in Example 28K);

C. 1-[2-(3-Aminophenyl)ethyl]-2,5$\alpha$-dimethyl-1,2,3,4,4a,5,10,10a-octahydro-3,5-ethenobenzo[g-]quinoline and 1-[2-(3-aminophenyl)ethyl]-2,5$\alpha$-dimethyl-1,2,3,4,4a,5,10,10a-octahydro-3,5-ethanobenzo[g]quinoline, by alkaline saponification, respectively, of 1-[2-(3-acetylaminophenyl)ethyl]-2,5$\alpha$-dimethyl-1,2,3,4,4a,5,10,10a-octahydro-3,5e-thenobenzo[g]quinoline and 1-[2-(3-acetyl-aminophenyl)ethyl]-2,5$\alpha$-dimethyl-1,2,3,4,4a,5,10,10a-octahydro-3,5-ethanobenzo[g]quinoline (described in Example 28R).

EXAMPLE 30

A solution of 88 g. (0.33 mole) of 2-(4-methoxybenzyl)-8-methylene-3-azabicyclo[3.3.1]non-6-en-4-one (described in Example 15A) was dissolved in a solution of 800 ml. of glacial acetic acid and 180 ml. of concentrated sulfuric acid, and the mixture stirred and heated on a steam bath for 1 hour. The mixture was then poured into four liters of an ice/water mixture. The gum which separated slowly solidified and was collected and recrystallized 3 times from DMF to give 4.3 g. of 7-methoxy-5$\alpha$-methyl-3,4,4a,5,10,10a-hexahydro-3,5-ethenobenzo[g]quinoline-2-(1H)-one, m.p. 268°–272°C.

EXAMPLE 31

A solution of 5.38 g. (0.02 mole) of 7-methoxy-5$\alpha$-methyl-3,4,4a,5,10,10a-octahydro-3,5-ethenobenzo[g-]quinoline-2-(1H)-one (described in Example 30) in 250 ml. of tetrahydrofuran was added slowly to a stirred suspension of 1.52 g. (0.04 mole) of lithium aluminum hydride in 108 ml. of tetrahydrofuran, and the mixture was heated under reflux for one and one half hours and then worked up in the manner described above in Example 12. The product was isolated in the form of the hydrochloride salt which was recrystallized from ethanol/diethyl ether to give 3.08 g. of 7-methoxy-5$\alpha$-methyl-1,2,3,4,4a,5,10,10a-octahydro-3,5-ethenobenzo[g]quinoline hydrochloride, m.p. 254°–255°C.

EXAMPLE 32

A solution of 18.0 g. (0.07 mole) of 7-methoxy-5$\alpha$-methyl-1,2,3,4,4a,5,10,10a-octahydro-3,5-ethenobenzo[g]quinoline hydrochloride (described in Example 31) in 200 ml. of ethanol was reduced with hydrogen over 1.8 g. of palladium-on-charcoal under a hydrogen pressure of about 55 pounds p.s.i. When reduction was complete, the product was worked up in the manner described above in Example 3 to give 3.6 g. of 7-methoxy-5α-methyl-1,2,3,4,4a,5,10,10a-octahydro-3,5-ethanobenzo[g]quinoline, m.p. 82°–84°C. (from hexane).

each case, for the hydrochloride salts unless noted otherwise. The nature of the starting material and final product, whether the 3,5-etheno compounds of formula IIIa or the 3,5-ethano compounds of formula IIIb, is indicated by the designations IIIa and IIIb, respectively.

Table 34

| Example | $R_1$ | Wt.S.M. | Wt.Prod. | m.p. (°C.) | Solvent |
|---|---|---|---|---|---|
| 34B (IIIa) | $C_6H_5CH_2CH_2$ | 4.82 (base) | 5.4 | 190–192 | ethanol/ether |
| 34C (IIIb) | $CH_2=CHCH_2$ | 6.5 (HBr) | 5.3 | 238–241 | ethanol/ether |
| 34D (IIIb) | $C_6H_5CH_2CH_2$ | 6.49 (HBr) | 5.1 | 259–262 | ethanol |
| 34E (IIIa) | $C_3H_7$ | 4.82 (base) | 3.8 (a) | 210–211 (a) | $CH_3CN$/ether |
| 34F (IIIb) | $C_3H_5$—$CH_2$ (b) | 6.49 (HBr) | 2.5 | 252 | ethanol/ether |
| 34G (IIIb) | $C_3H_7$ | 6.49 (HBr) | 3.1 | 260–264 | ethanol/ether |

(a) Methanesulfonate salt
(b) Cyclopropylmethyl

EXAMPLE 33

A. A solution of 12.0 g. (0.047 mole) of 7-methoxy-5α-methyl-1,2,3,4,4a,5,10,10a-octahydro-3,5-ethenobenzo[g]quinoline hydrochloride (described in Example 31) in 60 ml. of 48% hydrobromic acid was refluxed and stirred for 15 minutes, then cooled and worked up in the manner described above in Example 17. The product was isolated in the form of the free base to give 5.7 g. of 7-hydroxy-5α-methyl-1,2,3,4,4a,5,10,10a-octahydro-3,5-ethenobenzo[g]quinoline, m.p. 298°–310°C. (from DMF);

B. Following a procedure similar to that described in Example 33A, 12.5 g. (0.049 mole) of 7-methoxy-5α-methyl-1,2,3,4,4a,5,10,10a-octahydro-3,5-ethanobenzo[g]quinoline (described in Example 32) was reacted with 62 ml. of 48% hydrobromic acid, and the product, in the form of the hydrobromide salt, was recrystallized from water to give 5.6 g. of 7-hydroxy-5α-methyl-1,2,3,4,4a,5,10,10a-octahydro-3,5-ethanobenzo[g]quinoline hydrobromide, m.p. 305°–311°C.

EXAMPLE 34

A. A mixture of 4.8 g. (0.02 mole) of 7-hydroxy-5α-methyl-1,2,3,4,4a,5,10,10a-octahydro-3,5-ethenobenzo[g]quinoline (described in Example 33A), 1.7 g. (0.02 mole) of sodium bicarbonate and 1.9 ml. (0.022 mole) of allyl bromide in 50 ml. of DMF was heated with stirring under reflux for one hour and then worked up in the manner described above in Example 7A. The product was isolated in the form of the hydrochloride salt which was recrystallized from ethanol/diethyl ether to give 2.6 g. of 1-allyl-7-hydroxy-5α-methyl-1,2,3,4,4a,5,10,10a-octahydro-3,5-ethenobenzo[g]quinoline hydrochloride, m.p. 246°–248°C.

Following a procedure similar to that described in Example 34A, using the 7-hydroxy-5α-methyl-1,2,3,4,4a,5,10,10a-octahydro-3,5-ethenobenzo[g]quinoline or the 7-hydroxy-5α-methyl-1,2,3,4,4a,5,10,10a-octahydro-3,5-ethanobenzo[g]quinoline described in Examples 33A and 33B, respectively, and an appropriate alkylating agent, $R_1$-Hal, there are prepared the corresponding 1-$R_1$-7-hydroxy-5α-methyl-1,2,3,4,4a,5,10,10a-octahydro-3,5-ethenobenzo[g]quinolines and 1-$R_1$-7-hydroxy-5α-methyl-1,2,3,4,4a,5,10,10a-octahydro-3,5-ethanobenzo[g]quinolines of formulas IIIa and IIIb, respectively, in Table 34 below where, in each instance, $R'_2$, and $R_3$ are hydrogen; Q is $H_2$; $R_2$ is HO; and $R_4$ is $CH_3$. The yields of products and the melting points are given, in

EXAMPLE 35

A. A mixture of 4.82 g. (0.02 mole) of 7-hydroxy-5α-methyl-1,2,3,4,4a,5,10,10a-octahydro-3,5-ethenobenzo[g]quinoline (described in Example 33A), 1.6 ml. (0.02 mole) of 37% aqueous formaldehyde and 100 ml. of ethanol was reduced with hydrogen over 2 g. of palladium-on-charcoal using a Parr-shaking apparatus. When reduction was complete, the mixture was worked up in the manner described above in Example 3 and the product isolated in the form of the hydrochloride salt to give 3.6 g. of 1,5α-dimethyl-7-hydroxy-1,2,3,4,4a,5,10,10a-octahydro-3,5-ethenobenzo[g]quinoline hydrochloride, m.p. 302°–305°C. (from ethanol/diethyl ether);

B. Following a procedure similar to that described in Example 35A, a mixture of 6.49 g. (0.02 mole) of 7-hydroxy-5α-methyl-1,2,3,4,4a,5,10,10a-octahydro-3,5-ethanobenzo[g]quinoline hydrobromide (described in Example 33B), 1.6 ml. (0.02 mole) of 37% aqueous formaldehyde and 2.8 ml. (0.02 mole) of triethylamine in 100 ml. of ethanol was reduced with hydrogen over 2 g. of palladium-on-charcoal and the product isolated in the form of the hydrochloride salt to give 2.8 g. of 1,5α-dimethyl-7-hydroxy-1,2,3,4,4a,5,10,10a-octahydro-3,5-ethanobenzo[g]quinoline hydrochloride, m.p. 318°C. (from water).

The compounds of formula I are generally active in primary analgesic screening tests [the acetylcholine-induced abdominal constriction (Ach) and the phenyl-p-quinone-induced writhing (PPQ) tests] and also in the rat tail flick radiant thermal heat analgesic test (Tail Flick Agon.). Data so obtained for the compounds, identified by reference to the preceding examples and expressed either in terms of the $ED_{50}$ (mg./kg., subcutaneous administration) or in terms of percent inhibition, are given below.

| Example | Ach | PPQ | Tail Flick Agon. |
|---|---|---|---|
| 16A | 1.7 | | 14±2 |
| 16C | 1.1 | | 11±1.0 |
| 16D | 7.4 | 64%/50 mg./kg. | Inact. |
| 16B | 0.3 | | 6.9±0.8 |
| 19A | 8.9 | | Inact. |
| 19C | 6.9 | | 64±12 |
| 20A | 1.6 | | 11±2.2 |
| 20B | 2.1 | | 10%/60 mg./kg. |
| 20C | 4.7 | 11 | Inact. |
| 20D | 16 | | |
| 20F | ~10 | | |

-continued

| Example | Ach | PPQ | Tail Flick Agon. |
|---|---|---|---|
| 24A | >25, <75 | | |
| 24B | 40%/75 mg./kg. 27%/25 mg./kg. | | Inact. |
| 26 | 2.5 | | ~60 |
| 25 | 6.5 | | Inact. |

The compounds of Examples 16D, 19A, 20D, 24A and 25 have also been found active in the phenazocine tail flick antagonist test, the $ED_{50}$ (subcutaneous administration) for those species being, respectively, 24, 0.088, 0.046, 0.27 and 0.025 mg./kg.

The compounds of formulas IIIa and IIIb are generally active in the same primary analgesic screening tests, the acetylcholine-induced abdominal constriction and the phenyl-p-quinoneinduced writhing tests. Data so-obtained is given below.

| Example/Formula | Ach | PPQ |
|---|---|---|
| 28A/IIIa | 2.7 | |
| 28A/IIIb | 17 | |
| 28B/IIIa | 1.6 | 20 |
| 28C/IIIa | 4.1 | 36 |
| 30/IIIa | Inact. | |
| 31/IIIa | 4.6 | 17 |
| 32/IIIb | 5.1 | 13 |
| 33A/IIIa | 3.5 | Inact. |
| 34A/IIIa | 11 | |
| 34B/IIIa | 1.4 | 10 |
| 34C/IIIb | 12 | Inact. |
| 34D/IIIb | 16 | Inact. |
| 34E/IIIa | 4.5 | |
| 34F/IIIb | 3.2 | 100%/70 mg./kg. 43%/35 mg./kg. |
| 34G/IIIb | 13 | 43 |
| 35A/IIIa | 1.9 | 23 |
| 35B/IIIb | 3.0 | 23 |

I claim:
1. A compound having the formula

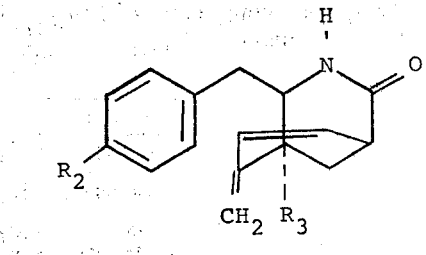

where $R_2$ is hydrogen or lower-alkoxy and $R_3$ is hydrogen or lower-alkyl.

2. A compound according to claim 1 having the formula

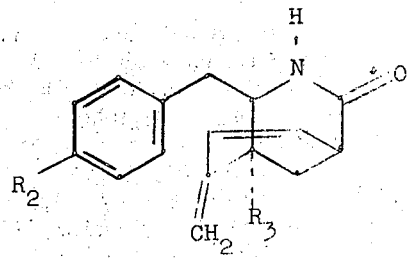

where $R_2$ is hydrogen or lower-alkoxy and $R_3$ is hydrogen.

3. 2-(4-Methoxybenzyl)-8-methylene-3-azabicyclo[3.3.1]non-6-en-4-one according to claim 2.

* * * * *